US012802816B2

(12) United States Patent
H.

(10) Patent No.: US 12,802,816 B2
(45) Date of Patent: Nov. 17, 2026

(54) EVALUATING A SEQUENCE OF ENTRIES TO PREDICT A FUTURE EVENT

(71) Applicant: MatrixCare, Inc., Bloomington, MN (US)

(72) Inventor: Samsudhin H., Chennai (IN)

(73) Assignee: MatrixCare Inc., Bloomington, MN (US)

( * ) Notice: Subject to any disclaimer, the term of this patent is extended or adjusted under 35 U.S.C. 154(b) by 981 days.

(21) Appl. No.: 17/656,305

(22) Filed: Mar. 24, 2022

(65) Prior Publication Data

US 2023/0214726 A1 Jul. 6, 2023

Related U.S. Application Data

(60) Provisional application No. 63/266,394, filed on Jan. 4, 2022.

(51) Int. Cl.

| | |
|---|---|
| ***G16H 40/20*** | (2018.01) |
| ***G06F 18/2415*** | (2023.01) |
| ***G06F 18/28*** | (2023.01) |
| ***G06N 3/045*** | (2023.01) |
| ***G06N 3/08*** | (2023.01) |
| ***G06N 5/01*** | (2023.01) |
| ***G06N 7/01*** | (2023.01) |
| ***G06N 20/00*** | (2019.01) |
| ***G06N 20/10*** | (2019.01) |
| ***G06N 20/20*** | (2019.01) |
| ***G16H 10/60*** | (2018.01) |
| ***G16H 20/10*** | (2018.01) |
| ***G16H 40/40*** | (2018.01) |
| ***G16H 50/20*** | (2018.01) |
| ***G16H 50/30*** | (2018.01) |
| ***G16H 50/70*** | (2018.01) |

(52) U.S. Cl.

CPC ......... *G16H 50/20* (2018.01); *G06F 18/2415* (2023.01); *G06F 18/28* (2023.01); *G06N 20/20* (2019.01); *G16H 20/10* (2018.01)

(58) Field of Classification Search

CPC ........ G16H 50/20; G16H 20/10; G06N 20/20; G06F 18/28; G06F 18/2415

See application file for complete search history.

(56) References Cited

U.S. PATENT DOCUMENTS

| | | | | | |
|---|---|---|---|---|---|
| 10,177,989 | B1 * | 1/2019 | Goyal | .................. | H04L 41/147 |
| 2017/0353477 | A1 * | 12/2017 | Faigon | .................. | G06F 21/554 |
| 2020/0342305 | A1 * | 10/2020 | Du | ......................... | G06N 20/10 |
| 2021/0327594 | A1 * | 10/2021 | Shukla | .................. | G06N 5/047 |

* cited by examiner

*Primary Examiner* — Abdullah Al Kawsar
*Assistant Examiner* — Gary Mac
(74) *Attorney, Agent, or Firm* — Patterson + Sheridan, LLP

(57) ABSTRACT

Embodiments herein describe predicting a future event using a sequence of entries. In one embodiment, the sequence of entries are first processed by a static model that includes a dictionary for translating each entry in the sequence to a weight. In one embodiment, these weights can then be combined to provide an input to a machine learning (ML) model. The model then predicts whether the likelihood a future event will occur.

20 Claims, 12 Drawing Sheets

300

| STATIC MODEL DICTIONARY | |
|---|---|
| ENTRIES (305) | WEIGHTS (310) |
| ENTRY A | 6.27 |
| ENTRY B | -2.49 |
| ENTRY C | -1.94 |
| ENTRY D | -0.73 |
| ENTRY E | 1.96 |
| ENTRY F | -1.94 |

*Fig. 3*

400

| RECORDS | | |
|---|---|---|
| ID | SEQUENCE OF ENTRIES | EVENT OCCURRED? |
| 1 | A, C, D, A, F | Y |
| 2 | C, B, F | N |
| 3 | A, A, E, B, A, E | Y |
| 4 | D, A, D, B, F, C, E | N |

*Fig. 4*

EVALUATING A SEQUENCE OF ENTRIES TO PREDICT A FUTURE EVENT

CROSS-REFERENCE TO RELATED APPLICATIONS

This application claims benefit of U.S. Provisional Application 63/266,394 filed on Jan. 4, 2022, titled "SYSTEMS AND METHODS FOR PREDICTING A FALL."

BACKGROUND

Field

Embodiments of the present invention generally relate to generating a static model which can be used to evaluate a sequence of data to predict whether an event will occur.

Description of the Related Art

Data sequences that are correlated to a specific event can arise in many different types of technical fields. One such field is diagnosis codes in the medical field where patients can be diagnosed with different ailments which can be correlated to a particular event, such as a fall. That is, a patient with a particular set of diagnosis may be more likely to experience a fall event in the future. As another example in the medical field, some combinations of medications may correspond to a particular event such a rare or unusual symptom. That is, the symptom may not occur when any one of the medications is prescribed to a patient, but may arise when a particular combination of medications is prescribed. In another example, a repair history of a vehicle may indicate whether a future event, such as a part failing, will happen in the near future.

It is difficult to identify when a data sequence (e.g., diagnosis codes, medication history, repair history, and the like) is correlated with a particular future event. It often requires many man hours for a person to review historical data and identify the correlation. Further, the relationship between the labeled data and the event may not always occur—i.e., a particular combination of diagnosis codes merely indicates an increased likelihood that a patient will experience a fall event, but does not guarantee the fall event will occur—which makes identifying the correlation between labeled data and a particular event more difficult to discover.

SUMMARY

One embodiment herein is a method that includes receiving a plurality of historical records, each comprising a sequence of entries and an indication whether an event occurred. For every entry in the sequences of entries, the method includes selecting a first entry in the sequences of entries, generating, for every record of the plurality of historical records, a ratio of a number of times the first entry is in the sequence of entries versus a total number of entries in the sequence, summing the ratios of the plurality of records indicating that the event did occur to yield a first summation (X), summing the ratios of the plurality of records indicating that the event did not occur to yield a second summation (Y), and generating a weight for the first entry using X/Y−Y/X. The method also includes storing weights for the entries of the sequences of entries in a static model dictionary, and using the static model dictionary to at least one of (i) train a first machine learning (ML) model or (ii) provide input to a second ML model to predict whether the event will occur.

Another embodiment herein is a method that includes providing a static model dictionary storing weights, each corresponding to a different entry; receiving a record comprising a sequence of entries; converting each entry in the sequence of entries to a weight using the static model dictionary; combining the weights to yield a combined weight; and using the combined weight to at least one of (i) train a first machine learning (ML) model or (ii) provide input to a second ML model to predict whether an event will occur.

Another embodiment herein is a non-transitory computer readable medium comprising instructions to be executed in a processor, the instructions when executed in the processor perform an operation. The operation comprising providing a static model dictionary storing weights, each corresponding to a different entry; receiving a record comprising a sequence of entries; converting each entry in the sequence of entries to a weight using the static model dictionary; combining the weights to yield a combined weight; and using the combined weight to at least one of (i) train a first machine learning (ML) model or (ii) provide input to a second ML model to predict whether an event will occur.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, may admit to other equally effective embodiments.

FIG. 3 illustrates a static model dictionary, according to one embodiment.

FIG. 4 illustrates records containing a sequence of entries, according to one embodiment.

To facilitate understanding, identical reference numerals have been used, where possible, to designate identical elements that are common to the figures. It is contemplated that elements and features of one embodiment may be beneficially incorporated in other embodiments without further recitation.

DETAILED DESCRIPTION

Embodiments herein describe predicting a future event using a sequence of entries. In one embodiment, the sequence of entries are first processed by a static model that includes a dictionary for translating each entry in the sequence to a weight. These weights can then be combined to provide an input to a machine learning (ML) model. The model then predicts whether the likelihood a future event will occur. As discussed above, a patient can have multiple diagnosis codes (e.g., a sequence of entries) stored in their electronic health record (EHR). The static model can translate these entries into numerical weights which are then input into the ML model to determine whether a future event will occur such as falling, developing a new symptom for a current ailment, or developing a new ailment (e.g., bed sores).

As another example, a repair technician may record a repair history as a sequence of entries for a vehicle, power plant, robot, assembly line, and the like. A static model can use a dictionary to translate the entries into weights which are then input into the ML model to determine the likelihood of a future event such as part failure, loss of service, defects in manufactured goods, and the like.

In one embodiment, the static model dictionary can be generated using historical records containing a sequence of entries and an indication whether a particular event did, or did not, occur. For example, the system can collect medical records for past patients that list their diagnosis codes and indicate whether a particular event (e.g., a fall, new symptom, or new ailment) occurred. These records can then be processed to determine a weight for each diagnosis code, where that weight indicates whether the diagnosis code is a good indicator that the event will, or will not, occur in the future. For example, a large, positive weight may indicate the diagnosis code is strong indicator that the event will occur in the future, while a large, negative weight is a strong indicator that the event will not occur in the future. A small positive or negative weight (or a zero weight) may indicate that the diagnosis code is not a strong indicator either way—i.e., the diagnosis code is not a strong indicator that the event will, or will not, occur in the future. These weights can then be stored in the static model dictionary so that, during operation, a different sequence of entries can be translated into weights which are then input into the ML model to make a prediction. Further, the weights in the static model dictionary can be used to train the ML model.

Figure 1:
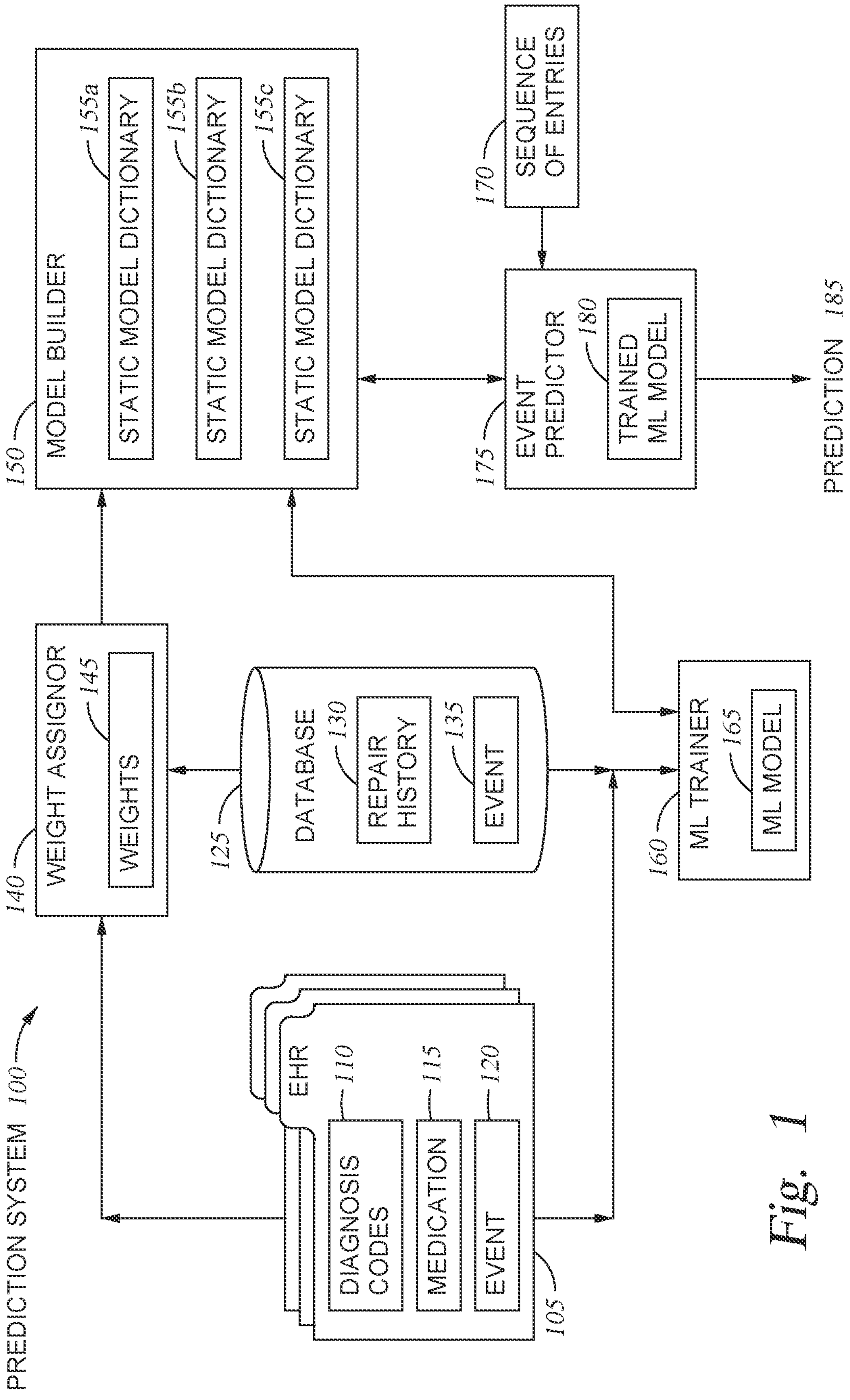
FIG. 1 illustrates a workflow for predicting events using a static model dictionary, according to one embodiment.

FIG. 1 illustrates a workflow of a prediction system 100 for predicting events using a static model dictionary, according to one embodiment. The prediction system 100 receives historical records that a weight assignor 140 and a model builder 150 use to create static model dictionaries 155 that can be used with different types of sequences. In this example, the historical records include EHRs 105 that include one or more sequences of entries. In FIG. 1, the EHRs 105 include two different sequences of entries: diagnosis codes 110 and medications 115. The diagnosis codes 110 can include the diagnoses for a patient over a time period (e.g., the life of the patient, since the person was admitted into a hospital or care facility, or the diagnoses made in the last year). In one embodiment, the diagnosis codes 110 are standardized using a medical classification. One such classification is the International Statistical Classification of Diseases and Related Health Problems (ICD) which is a medical classification list that includes codes for diseases, signs and symptoms, abnormal findings, complaints, social circumstances, and external causes of injury or diseases. However, this is just one medical classification or standard that can be used to standardize the diagnosis codes 110.

The medications 115 can be the current medications taken by the patient, or they can be a list of medications taken by the patient over a time period. The medications 115 may also be assigned according to a standard (e.g., a medical classification that provides medication codes) or by using agreed upon names for a medication or treatment. By using standardized codes or names for the medications 115 and the diagnosis codes 110, these entries are more easily assigned weights by the weight assignor 140 as discussed in more detail below.

The system 100 also includes a repair database 125 which stores a repair history for a particular apparatus (e.g., a vehicle, power plant, assembly line, robot, etc.). The repair history 130 includes a sequence of entries for the apparatus which can indicate the different repair actions or different maintenance issues that occurred over a time frame (e.g., the life of the apparatus or over the last year). The entries in the repair history 130 can be described using a defined standard (e.g., repair codes or maintenance codes). For example, the repair history 130 can include Diagnostic Trouble Codes (DTC codes) or On-board Diagnostics (OBD) which are standards used to diagnosis issues in an automobile. But the embodiments herein can be used with standards corresponding to any suitable type of apparatuses or systems.

Both the EHRs 105 and the repair database 125 store an indication whether a particular event occurred. For example, the EHR 105 for the patient can indicate an event 120 such as falling, developing a new symptom, or developing a new ailment. The repair database 125 can indicate, for each apparatus being tracked, if an event 135 such as part failure, loss of service, or defects in manufactured parts occurred. The system 100 may track one event, or multiple events. For example, the system 100 may also be used to predict only whether a patient has a high likelihood of falling, or the system 100 may predict whether a patient is likely to fall and develop a new ailment (e.g., bed sores).

The weight assignor 140 receives the sequence of entries (e.g., the diagnosis codes 110, the medications 115, or the repair history 130) and the event 120 or the event 135 and assign weights 145 to each entry in the sequence. That is, the weight assignor 140 can use an algorithm (which is described in detail in FIG. 5) to generate a weight 145 (e.g., a numerical value) for each entry in the sequence. For example, the weight assignor 140 may assign a weight 145 to each diagnosis code 110, or each medication 115, or each repair or maintenance code in the repair history 130.

In one embodiment, the weight 145 indicates whether the entry in the sequence is strongly or weakly correlated to the event 120 or the event 135. For example, assigning a large, positive weight 145 to a particular entry (e.g., a particular diagnosis code, s particular medication, or s particular maintenance code) means the entry strongly suggests the future event will occur. In contrast, assigning a large, negative weight 145 to a particular entry means the entry strongly suggests the future event will not occur. However, assigning a small, negative or positive weight to a particular entry means the entry is not a strong indicator of whether the future event will, or will not, occur. However, using negative and positive weights 145 is just one example of assigning weights to indicate the likelihood of future events.

The model builder 150 receives the weights 145 from the weight assignor 140 and uses the weights 145 to generate static model dictionaries 155. In this example, the model builder 150 has generated three static model dictionaries 155A-C which correlate to the three different types of sequences of entries shown on the left side of FIG. 1. For example, the static model dictionary 155A can store the weights 145 assigned to the diagnosis codes 110, the static model dictionary 155B can store the weights 145 assigned to the medications 115, and the static model dictionary 155C can store the weights 145 assigned to the repair history 130. As an example, the static model dictionary 155A can have an entry for each diagnosis code defined in a standard (e.g., the ICD codes) and the corresponding weight 145 for that code which was assigned by the weight assignor 140. The static model dictionaries 155B and 155C can have the same information for the medications 115 and the DCT or OBD codes of the repair history 130. In this manner, the model builder 150 can generate a static model dictionary 155 for different types of sequences—e.g., sequences of diagnosis code, sequences of medications, sequences of repair or maintenance codes, and the like.

The system 100 illustrates using the static model dictionaries 155 to train a ML model 165 (e.g., a neural network or other suitable type of ML model). As shown, a ML trainer 160 can receive the sequence of entries and events 120, 135 from the EHR 105 and the repair database 125. For example, if the ML trainer 160 is training the ML model 165 to predict a fall, the ML trainer 160 can retrieve the diagnosis codes 110 and the event 120 from EHRs 105 for a plurality of patients. However, the diagnosis codes 110 are typically in a format that is unsuitable to be used to train the ML model 165. Instead, the ML trainer 160 can use the static model dictionary 155 corresponding to the diagnosis codes 110 (e.g., the dictionary 155A) to translate the diagnosis codes 110 into the weights 145. The ML trainer 160 can then train the ML model 165 using the weights 145, rather than using the diagnosis codes 110. For example, a patient's EHR 105 may include a sequence of ICD codes such as: N39.0, R52, I10, F32.9, and E78.5. Using the dictionary 155A, the ML trainer 160 can translate these ICD codes into their corresponding numerical weights 145, e.g., 1.8, −2.1, 0.1, −0.7, 4.2. In one embodiment, the ML trainer 160 also combines these weights (e.g., averages them) to result in a final weight for the patient. This final weight along with the indication whether the event 120 occurred to the patient (e.g., whether the patient did, or did not fall) can be then be input into the ML model 165 for training. The ML trainer 160 can repeat this process using multiple EHRs 105 in order to generate sufficient annotated training data for training the ML model 165.

A similar process can be performed to train the ML model 165 to predict other types of events using the medications 115 or the repair history 130. That is, these sequences of entries can be converted to weights using the static model dictionaries 1558 and 155C to generate training data. While FIG. 1 illustrates a single ML model 165, the system 100 may train a different ML model for each event it wants to predict—e.g., a fall, developing a new symptom, part failure, loss of service, etc. The ML trainer 160 may use only one type of sequence (e.g., only the diagnosis codes 110) to train the ML model 165 to predict a particular future event (e.g., a fall), or use multiple types of sequences (e.g., both the diagnosis codes 110 and the medications 115) to train the ML model 165 to predict the future event (e.g., a fall). Training the ML model 165 is discussed in more detail in FIG. 2.

The prediction system 100 includes an event predictor 175 that uses a trained ML model 180 (e.g., a neural network or other suitable type of ML model) to predict whether a particular future event, or multiple future events, will occur. As shown, the event predictor 175 receives a sequence of entries 170 as an input. The event predictor 175 is tasked with predicting whether, based on the sequence of entries 170, a particular event (e.g., a fall, developing a new symptom, part failure, loss of service, etc.) will occur. The sequence of entries 170 can be any of the sequences discussed above such as diagnosis codes, prescribed medications, or a repair history. In one embodiment, the sequence of entries 170 can correspond to a single patient or one apparatus/system (e.g., a vehicle, power plant, assembly line, or robot). For example, a healthcare facility may want to know whether a particular patient is at risk for falling and send the diagnosis codes for that patient to the event predictor 175. Or a technician may want to know whether a power plant is likely to experience a loss of service in the near future and send the repair history of the power plant (e.g., maintenance codes) to the event predictor 175.

Like when training the ML model 165, the diagnosis codes, medications, or the maintenance codes may not be a suitable input for the ML model 180 (which may be the trained version of the ML model 165). As such, the event predictor 175 can use the static model dictionaries 155 to translate the sequence of entries 170 into the weights 145. These weights 145 can be combined (e.g., averaged) and input into the trained ML model 180 which then outputs a likelihood that a particular event (or multiple events) will occur. Thus, unlike the EHR 105 and the repair history 130 which store indicators whether the events 120, 135 did or did not occur, the sequence of entries 170 does not have an indicator of whether the event did occur. In this case, the event predictor 175 can use the trained ML model 180 to predict whether the event 120 or the event 135 is likely, or is unlikely, to occur. Using the event predictor 175 to predict whether an event (or events) is likely to occur using the sequence of entries 170 is discussed in more detail in FIG. 2.

Figure 2:
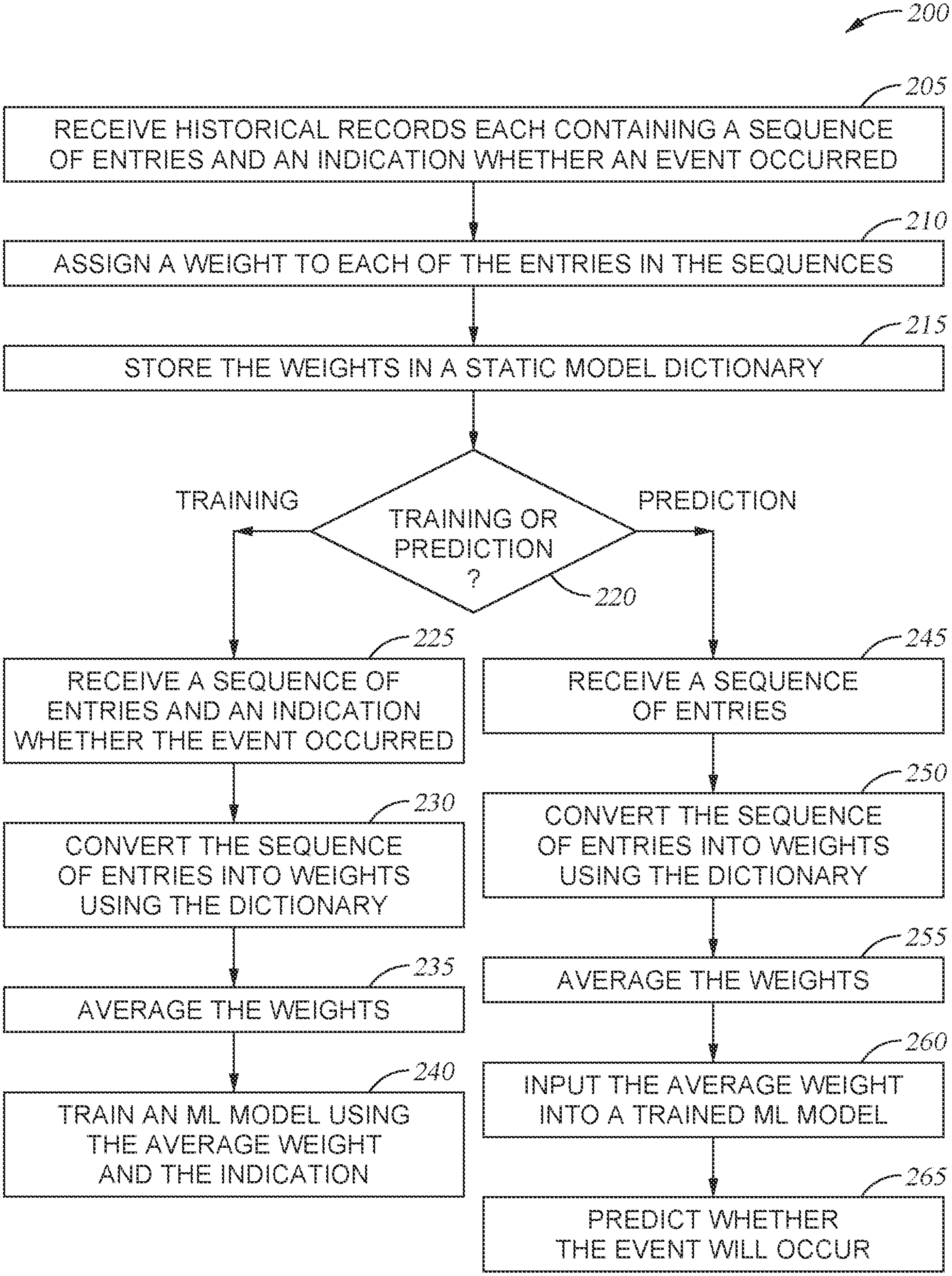
FIG. 2 is a flowchart for predicting events using a static model dictionary, according to one embodiment.

FIG. 2 is a flowchart of a method 200 for predicting events using a static model dictionary, according to one embodiment. At block 205, the prediction system (e.g., the prediction system 100 in FIG. 1) receives historical records each containing a sequence of entries and an indicator whether an event occurred. For example, the historical records can be EHRs (e.g., the EHRs 105 in FIG. 1) for a plurality of patients where each EHR includes a sequence of diagnosis codes. Alternatively or additionally, the EHRs can include a sequence of medications (e.g., the current medications assigned to the patients, or a list of recently prescribed medications). In yet another example, the historical records can include repair histories for a plurality of apparatuses or systems (e.g., vehicles, power plants, assembly lines, robots, etc.). Each repair history can include a sequence of maintenance or repair codes for the corresponding apparatus or system, listing the type of repairs performed on the apparatus or system, or the types of faults or errors occurred on the apparatus or system. However, these are just some examples of historical records. The embodiments herein can be used with any records that store a sequence of entries for a living organism (e.g., human, plant, animal), apparatus, or system. For instance, the embodiments herein could apply to medical records for a pet or livestock which store diagnosis codes or medications for that animal. Further still, the embodiments herein could be applied to historical records for a ticker in a stock market where the sequence of entries indicate whether the stock was up or down on multiple days.

Moreover, the embodiments herein are not limited to any particular type of events. For example, the historical records can include indications whether a patient fell, developed a new symptom, or developed a new ailment. As another example, the historical records can include indications whether an apparatus had a failed part, experienced a loss of service, or produced a defective product.

At block 210, a weight assignor in the prediction system (e.g., the weight assignor 140 in FIG. 1) assigns a weight to each entry in the sequences. For instance, if the sequence of entries is a list of ICD codes or maintenance codes, the weight assignor can use a technique to assign a weight to each of the codes. The details of one suitable technique for assigning weights is discussed in FIG. 5.

At block 215, a model builder (e.g., the model builder 150 in FIG. 1) stores the weights in a static model dictionary. For example, the weight assignor may assign a weight to every ICD code, where the weights are stored, along with the ICD codes in a static model dictionary. As discussed below, the static model dictionary can be used to translate ICD codes into weights that are more easily consumed or processed by ML models.

FIG. 3 illustrates one example of a static model dictionary 300, according to one embodiment. The static model dictionary 300 includes a left column storing entries 305 and a right column storing weights 310 that were assigned to those entries at block 210 of the method 200. In this example, the dictionary 300 stores six entries, Entries A-F, with their corresponding weights. For example, the Entries A-F may be diagnosis codes, medications, repair codes, maintenance codes, and the like.

In this example, the weights 310 assigned to each entry 305 indicates whether that entry 305 is strongly or weakly correlated to a particular event. For example, assigning a large, positive weight 310 a particular entry (e.g., a particular diagnosis code, particular medication, or particular maintenance code) means the entry 305 strongly suggests the future event will occur. In FIG. 3, Entry A has the largest positive weight 310 (6.27) indicating it is strongly correlated to the event occurring. Entry E also has a positive weight (1.96) but it is not as strongly correlated with the event occurring.

In contrast, assigning a large, negative weight to a particular entry means the entry strongly suggests the future event will not occur. For instance, Entry B as the most negative weight (−2.49) which means this entry is most strongly correlated with the event not occurring. However, assigning a small negative or a small positive weight to a particular entry means the entry is not a strong indicator whether the future event will, or will not, occur. For example, Entry D has a weight (−0.73) that is closest to zero, and thus, is not a good indicator of whether the event did, or did not, occur. Again, various techniques for determining the weights 310 are discussed in FIG. 5.

Returning to FIG. 2, at block 220, the method 200 determines whether a ML model is being trained, or whether an already trained ML model is being used to provide a prediction. If being used to train an ML model, the method 200 proceeds to block 225 where the ML trainer (e.g., the ML trainer 160 in FIG. 1) receives a sequence of entries and an indication whether the event occurred. For example, the ML trainer can receive the historical records described at block 205, an example of which is shown in FIG. 4.

FIG. 4 illustrates records 400 containing a sequence of entries, according to one embodiment. For example, the records 400 may be historical records that are used to train a ML model. As shown, the records 400 are identified using an ID (e.g., 1-4) and each includes a sequence of entries. Further, the records 400 indicate whether an event did, or did not, occur. For example, the records 400 may be EHRs, where each record is an EHR for a different patient. In that example, the sequence of entries may be a list of diagnosis codes or medications for that patient. In another example, the records 400 can be a repair history for four different apparatuses or systems (e.g., Vehicle 1, Vehicle 2, Vehicle 3, and Vehicle 4). The sequence of entries in each record can be the different repair operations performed on the apparatus, or the maintenance codes generated by the apparatus.

The event can be any event a ML model can be trained to detect, such as a fall, part failure, new ailment, loss of service, and the like. An indication of whether the event occurred may be stored in the records 400 as a separate entry, or natural language processing (NLP) or document scanning may be used to parse the record and determine whether the event did or did not occur. In this case, Records 1 and 3 indicate the event did occur while Records 2 and 4 indicate the event did not occur. Moreover, while FIG. 4 illustrates using historical records 400 to determine if one event occurred, the record 400 may track whether multiple events occurred (e.g., a predefined combination of events).

Notably, some of the records have repeated entries. For example, Record 1 has two A entries, Record 3 has three A entries and two E entries, and Record 4 has two D entries. These can be records for patients that have been diagnosed with the same ailment multiple times. Or these records can be for apparatuses that have had the same repair performed multiple times, or experienced the same error code multiple times. However, in other implementations, each of the records 400 may not have repeated entries.

Returning to FIG. 2, at block 230, the ML trainer converts (or translates) the sequence of entries into weights using the static model dictionary stored at block 215. Using the records 400 in FIG. 4 and the dictionary 300 in FIG. 3 as an example, the sequence of entries for Record 1 can be converted from Entries A, C, D, A, F into weights 6.27, −1.94, −0.73, 6.27, −1.94. As discussed above, converting the entries, which can be a sequence of codes, into numerical weights can convert the data into a format that is consumable by the ML model.

At block 235, the ML trainer averages the weights. Continuing the previous example, since there are five entries in the sequence, the weights determined at block 230 are summed and divided by five to yield the average weight (also referred to as the final weight or the combined weight). Doing so yields an average weight of approximately 1.59.

At block 240, the ML trainer trains the ML module using the average weight and the indication of the event. For example, the ML trainer can repeat blocks 225-235 for each of the historical records to determine the average weights for those records. The average weights along with the indications of whether the event occurred can then be used as annotated training data to train the ML model to predict the event.

Returning to block 220, if the method 200 is instead being used to make a prediction (e.g., the ML model has already been trained), the method 200 proceeds to block 245 where the event predictor (e.g., the event predictor 175 in FIG. 1) receives a sequence of entries. However, unlike the records 400 in FIG. 4, there is no indication of whether the event occurred. Instead, the event predictor is tasked with evaluating the sequence of entries and predicting whether the event will occur using the trained ML model. For example, the sequence of entries may be the diagnosis codes for a patient who is about to be released from a hospital and the healthcare provider wants to know whether the patient has a high likelihood of falling. Or the sequence of entries may be the diagnosis codes for a patient who may have recently been admitted into a healthcare facility and his doctor wants to know the patient's risk for developing bed sores. In yet another example, the sequence of entries may be the repair operations performed in the last year on a robot in an assembly line and a technician may want to know the likelihood the robot will experience a loss of service in the near future.

At block 250, the event predictor converts the sequence of entries into weights using the dictionary. This may be the same as block 230 where each of the entries in the sequence is converted into a corresponding weight using the static model dictionary (e.g., the dictionary 300 in FIG. 3).

At block 255, the event predictor averages the weights determined at block 250. This may be the same as block 235. However, this block may be skipped in some embodiments. In that case, the weights for each entry may be input directly into the ML model. Or in other embodiments the weights may be combined using a different technique than averaging, such as inputting a sum of the weights, or inputting the maximum or minimum weight.

At block 260, the ML model predicts whether the event will occur. For example, the ML model may output a percentage indicating the likelihood the event will occur in a particular time window (e.g., 60% likelihood the event will occur in one week, 80% likelihood the event will occur in two weeks, and 95% likelihood the event will occur in three weeks). In this manner, the method 200 indicates techniques for training a ML model to predict a particular event (or a combination of events) using weights assigned to each entry in a sequence of entries.

Figure 5:
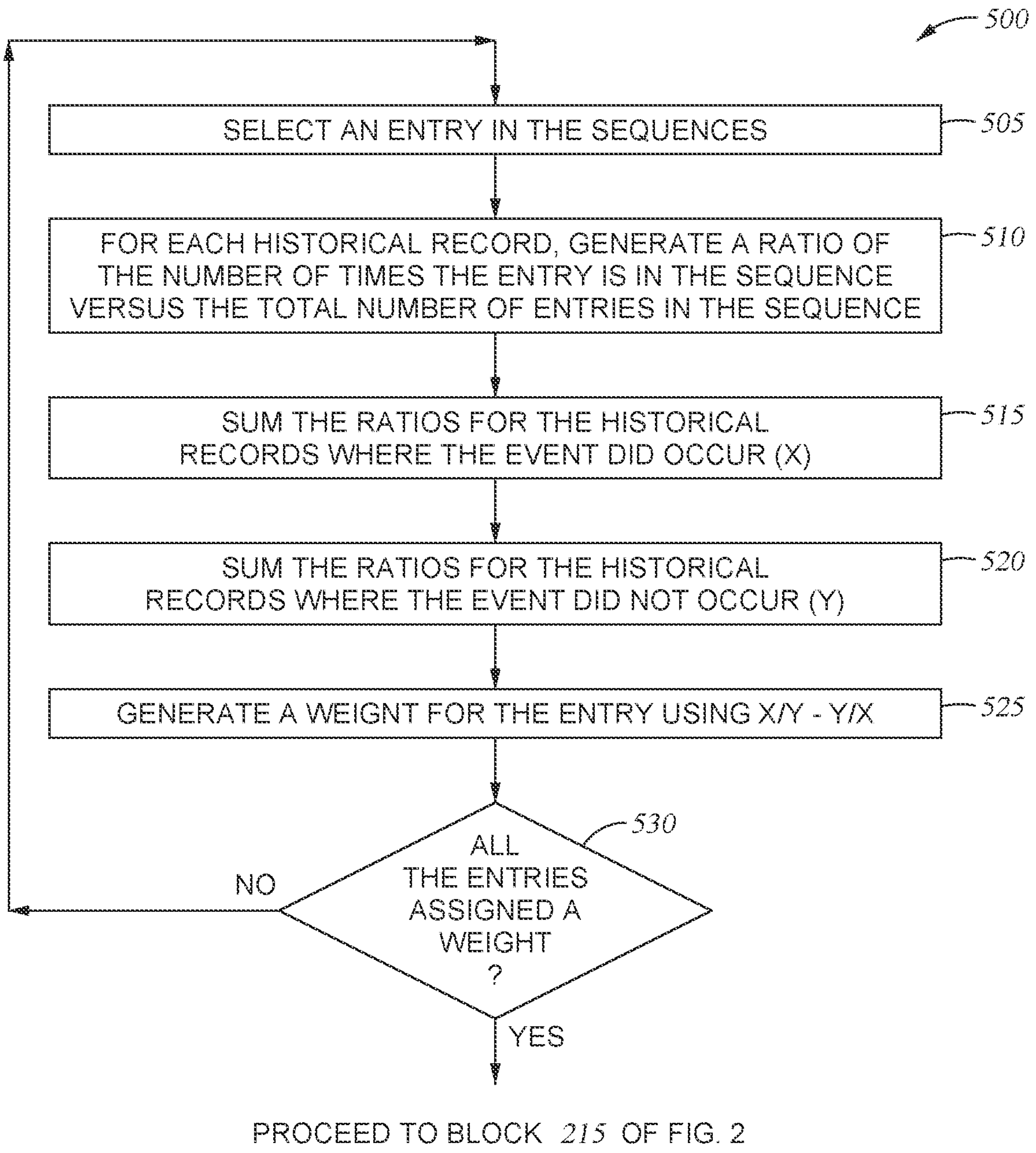
FIG. 5 is a flowchart for generating weights for a static model dictionary, according to one embodiment.

FIG. 5 is a flowchart of a method 500 for generating weights for a static model dictionary, according to one embodiment. In one embodiment, the method 500 describes techniques for assigning weights to sequences of entries, as discussed at block 210 of FIG. 2. But the embodiments herein are not limited to these techniques for assigning weights.

The method 500 may begin after block 205 of method 200 where the prediction system receives historical records each containing a sequence of entries. At block 505, the weight assignor selects an entry in the sequences. As discussed above, the sequence of entries may be lists of codes, such as diagnosis codes, repair codes, maintenance codes, and the like. In another examples, the sequences may be lists of medications or treatments currently prescribed to a patient. The weight assignor can select a particular one of the entries, e.g., a particular code, operation, or medication.

At block 510, for each historical record, the weight assignor generates a ratio of the number of times the entry is in the sequence versus the total number of entries in the sequence. Using the records 400 as an example, assuming the weight assignor has selected the Entry A, Record 1 has a ratio of 2/5 for this entry, Record 2 has a ratio of zero since it does not have any A entries, Record 3 has a ratio of 3/6 (or 1/2), and Record 4 has a ratio of 1/7. Thus, in this example, the weight assignor evaluates each record 400 to obtain a ratio associated with the Entry A.

At block 515, the weight assignor sums the ratios for the historical records where the event did occur, which is represented by the variable X. Continuing the example from above, as shown in FIG. 4 the Records 1 and 3 are records where the event did occur, so these ratios are summed to yield X=0.9 (i.e., 2/5+1/2).

At block 520, the weight assignor sums the ratios for the historical records where the event did not occur, which is represented by the variable Y. Continuing the example from above, as shown in FIG. 4 the Records 2 and 4 are records where the event did not occur, so these ratios can be summed to yield Y=0.14 (i.e., 0+1/7).

At block 525, the weight assignor generates a weight for the entry using Equation 1:

$$\frac{X}{Y} - \frac{Y}{X}$$

Here, X is the sum of the ratios for the historical records where the event did occur and Y is the sum of the ratios for the historical records where the event did not occur. Continuing the example, the weight for Entry A would be 6.27 (i.e., 0.9/0.14-0.14/0.9). This matches the weight stored in the static model dictionary 300 in FIG. 3 for Entry A.

At block 530, the weight assignor determines whether each entry in the sequences of entries has a weight assigned to it. If not, the method 500 then repeats to assign weights to those entries. For example, after assigning a weight to Entry A, the method 500 repeats to assign weights to Entries B-F. Once this is complete, the weight assignor now has weights for each entry in the sequences shown in FIG. 4. The method 500 can then proceed to block 215 of FIG. 2 to store the weights in the static model dictionary. As shown in FIG. 3, the weights for Entries A-F have been assigned based on the records 400 in FIG. 4 using the method 500. In this manner, the weight assignor can use these techniques in method 500 to assign weights to entries in different sequences in order to generate a static model dictionary. Once the dictionary is populated, these weights can then be used to generate training data to train a ML model as discussed in blocks 225-240 in the method 200, as well as convert other sequences of entries in numerical weights for making a prediction using a trained ML model as discussed in blocks 245-265 in the method 200.

In one embodiment, the weights determined using the method 500 can be used to make a prediction without training or using a ML model. For example, using the techniques described in FIG. 5, the weights can be evaluated to determine whether a particular sequence of entries indicate an event will likely occur, without using a ML model. As mentioned above, the weights for each individual entry shown in FIG. 3 can indicate whether the entry is strongly or weakly correlated to the event. For example, if performing the method 500 results in a large, positive weight for the currently selected entry, this means that entry is strongly correlated to the event occurring. A large, negative weight means the entry is strongly correlated to the event not occurring. Small negative and positive weights means the entry is not strongly correlated to the event occurring or not occurring. Given this, when the prediction system receives a sequence of entries (e.g., Entries A, B, F, E, C, B), the system can perform the blocks 245-255 in the method 200 to convert the entries into weights and then combine (e.g., average) the weights. In this example, using the dictionary 300, the Entries A, B, F, E, C, B can be converted into weights 6.27, −2.49, −1.94, 1.96, −1.94, −2.49 which when averaged yield a combined weight of −0.105. The sign and magnitude of the combined weight indicates whether the record is strongly correlated to the event or not. In this case, since the combined weight is close to zero, it is weakly correlated to the event, and thus, the prediction system may indicate it is uncertain whether the event will or will not occur (e.g., it cannot predict with any certainty whether the event will or will not occur). In contrast, if combining the weights for a sequence of entries yields a large, positive weight, the prediction system can indicate it is very likely the event will occur. If combining the weights for a sequence of entries yields a large, negative weight, the prediction system can indicate it is very likely the event will not occur. In this manner, the prediction system can use the static model dictionary and blocks 245-255 of method 200 to make a prediction without using a ML model.

Fall Prediction

While the embodiments discussed above are not limited to fall prediction, the discussion that follows describes using these techniques to predict the likelihood a patient will experience a future fall. Many of the techniques described below can also be applied to predict other future events such as the appearance of new symptoms, new ailments, part failure, loss of service, and the like.

Figure 6A:
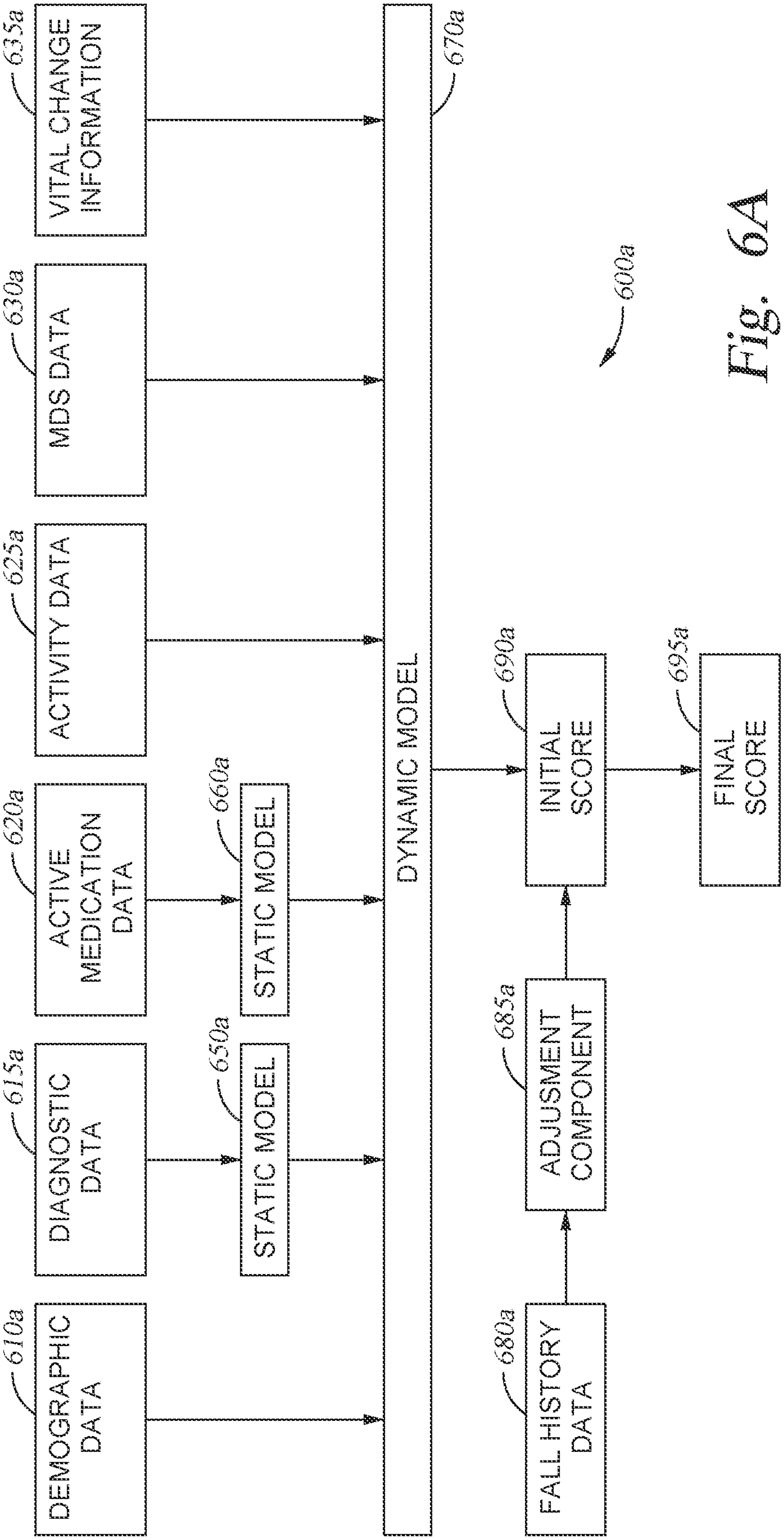
FIG. 6A is a machine learning training architecture, according to one or more implementations of the present disclosure.

FIG. 6A illustrates an architecture of an algorithm 600*a*, e.g. a machine learning training algorithm, that can train an algorithm to predict a fall of an individual. In one or more implementations, the architecture includes any suitable software and/or hardware units necessary to carry out the logic and/or flow of operations of the architecture 600*a*. In one or more implementations, the architecture 600*a* is the basis for training fall risk algorithm and can be stored in a memory of an overall computer system and can be implemented by one or more computer processors. In one or more implementations, any other suitable system or component described herein can be configured to execute algorithm 600*a*. As shown, and pursuant to one or more implementations, algorithm 600*a* includes a machine learning algorithm or model 670*a* for training. In one or more implementations, the algorithm utilizes data with respect to one or more individuals, where the received data, to train the algorithm 670*a* and, thereafter, other incoming data can be used to output one or more scores 690*a* that are an initial prediction of whether or not an individual can fall. The data associated with training can be demographic data 610*a*, diagnostic data 615*a*, medication data 620*a*, including active medication data, activity data 625*a*, MDS data 630*a*, and vital change information data 635*a*, where data 610*a*, 615*a*, 620*a*, 630*a*, and 635*a* can be as described above with reference to other implementations, where the data can be related to one or more individuals N (e.g. nursing home facility patients, hospital patients, etc.) as referenced with respect to other implementation as described above, and where the data sources can further be based in whole or in part on predetermined forms as described herein.

The machine learning algorithm 670*a* can be any suitable machine learning model, including but not limited to a static model, dynamic model, hybrid model, or any other suitable machine learning model.

As used herein, a "static" model or component refers to any one of: i) a pre-determined equation that receives an input of data, requires no training and produces a static factor that can adjust a weight associated with another model or component of a mode, ii) a pre-determined equation that receives data, requires no training and produces a static factor that can adjust a score outputted by another model, iii) a pre-determined equation that receives data, requires no training and produces a static factor that can adjust or modify a score outputted by another model (including a dynamic model), iv) a statically trained machine learning model that receives as data for training and produces a static, i.e. non-variable, factor that can adjust or affirmatively determine a weight associated with another model, where the adjusted weight remains unaltered during processing by the another model (even if other weights in the model are variable),) a statically trained machine learning model that receives as an input of data for training and produces a static, i.e. non-variable factor that can adjust a score outputted by another model (including a dynamic model), or vi) a combination of the previously mentioned. In one or more implementations, a "statically trained model" is a model that can be trained using any suitable machine learning technique, but requires no further training once initially trained, e.g. after a certain number of iterations of any suitable machine learning techniques such as backpropagation.

As used herein, a "dynamic" model or component refers to any one of: i) a model that has one or more weights that are variable during application of the model, ii) a model that receives continuous training or updating as it is applied, or iii) a combination of the previously mentioned.

In one or more implementations, as shown, machine learning algorithm 670*a* is a dynamic model in the form of a neural network. In one or more implementations, algorithm 600*a* includes a static component 650*a* and a static component 660*a*, which can be determined using any suitable technique as described herein and executed by any suitable component of a computer system. In one or more implementations, static component 650*b* and static component 660*b* are predetermined equations based on the ratio of individual diagnosis/medication that contributed to a fall event, subtracted by a ratio of individual diagnosis/medication contributed for a not fall event. In one or more implementations, static component 650*b* and static component 660*b* are based on the Equation 2:

$$(\text{Fall Count}/\text{Not Fall County})-(\text{Not Fall Count}/\text{Fall Count})$$

In one or more implementations, a processor can be configured to receive data and execute the operations associated with the static components where the static components 650 and 660 can be stored in memory and then integrated, upon execution, as part of fall risk algorithm.

In one or more implementations, the dynamic machine learning algorithm 670*a* directly receives input from data 610*a*, 620*a*, 625*a*, 630*a*, and 635*a*. In one or more implementations, static components 650*a* and 660*a* process, respectively, data from data sources 615*a* and 620*a*. In one or more implementations, the static components 650*a* and 660*a* form a relational matrix or table associated with the data inputs from sources 615*a* and 620*a*, apply Equation 2 to each row of the table, and generate one or more static weights in association therewith; thereafter, for each particular data type, the weights are averaged and are stored as a static dictionary to be inputted into the dynamic model 670*a* for training.

In one or more implementations, the initial weights of the model 670*a*, prior to initializing training, can be a randomly selected or can also be based on a probabilistic and deviation technique from fall and non-fall events in relation to those data points. In one or more implementations, the initialized weights can include a calculated weight bias and/or calculated weights based on any suitable initialization technique.

In one or more implementations, once initial weights are set for the model 670*a*, the model training can commence. In one or more implementations, the dynamic model 670*a*, e.g. neural network, receives as a direct input data from data sources 610*a*, 625*a*, 630*a*, and 635*a*, and the outputs of static components 650*a* and 660*a* (which include the processing of data from sources 615*a* and 620*a*, e.g. static weight averages from the static dictionary associated therewith). In one or more implementations, the training of model with the inputted data and outputs from the static components can include any suitable training techniques for training a dynamic model, including modulating and adjusting weights and biases in the input data, and in deeper levels of a deep learning algorithm (e.g., by back propagation methods) such that the prediction of a fall prediction becomes increasingly accurate. For example, the training described in FIGS. 1 and 2 may be used.

In one embodiment, a deviation from the fall prediction score and the prediction from the algorithm as it is trained is minimized to an acceptable minimum value. For example, the model can be validated with a Root Mean Squared Error on train/test ratio 70:30 (i.e., 70% of the data is used to train the model and 30% of the data is used to test the model). In one or more implementations, a processor can be configured to receive data and execute the operations indicated above to facilitate the training of machine learning algorithm 670*a*, and thereafter, machine learning algorithm can be stored in memory and then integrated, upon execution, as part of fall risk algorithm.

In one or more implementations, during training, the machine learning model 670*a*, produces one or more initial scores related to fall prediction, e.g. score 690*a*. In one or more implementations, the one or more initial scores 690*a*, are adjusted by an adjustment component 685*a*. In one or more implementations, the adjustment component 685*a* can be a static component, where the static component 685*a* is a predetermined equation or factor that adjusts the score outputted by machine learning model 670*a*. In one or more implementations, one of the most important indicators as to whether or not an individual will fall in the future is whether that individual has fallen in the past and the duration since the last fall. As such, in one or more implementations, the adjustment component 685*a* received fall history data 690, e.g. based on a fall history of one or more individuals, and applies and equation, e.g. Equation 3, to the initial score 690*a* to determine generate a final score 695*a*. Equation 3:

$$Nf*2\%$$

Where "Nf" stands for the number of fall counts within a predetermined time range associated with one or more individuals. In one or more implementations, the adjustment component utilizes an equation that multiplies the number of days Nd since the last time an individual fell by a predetermined percentage factor, where the percentage factor can be determined by applying probabilistic and deviation techniques on data associated with the falls of other individuals. In one or more implementations, an equation in conjunction with thresholding operations. In one or more implementations, since the adjustment factor produced or generated by the adjustment component is based on a static equation, the adjustment component is itself a static component that does not require training. In one or more implementations, a processor can be configured to receive data and execute the operations indicated above to produce the adjustment component, where the adjustment component be stored in memory and then integrated, upon execution, as part of fall risk algorithm.

Figure 6B:
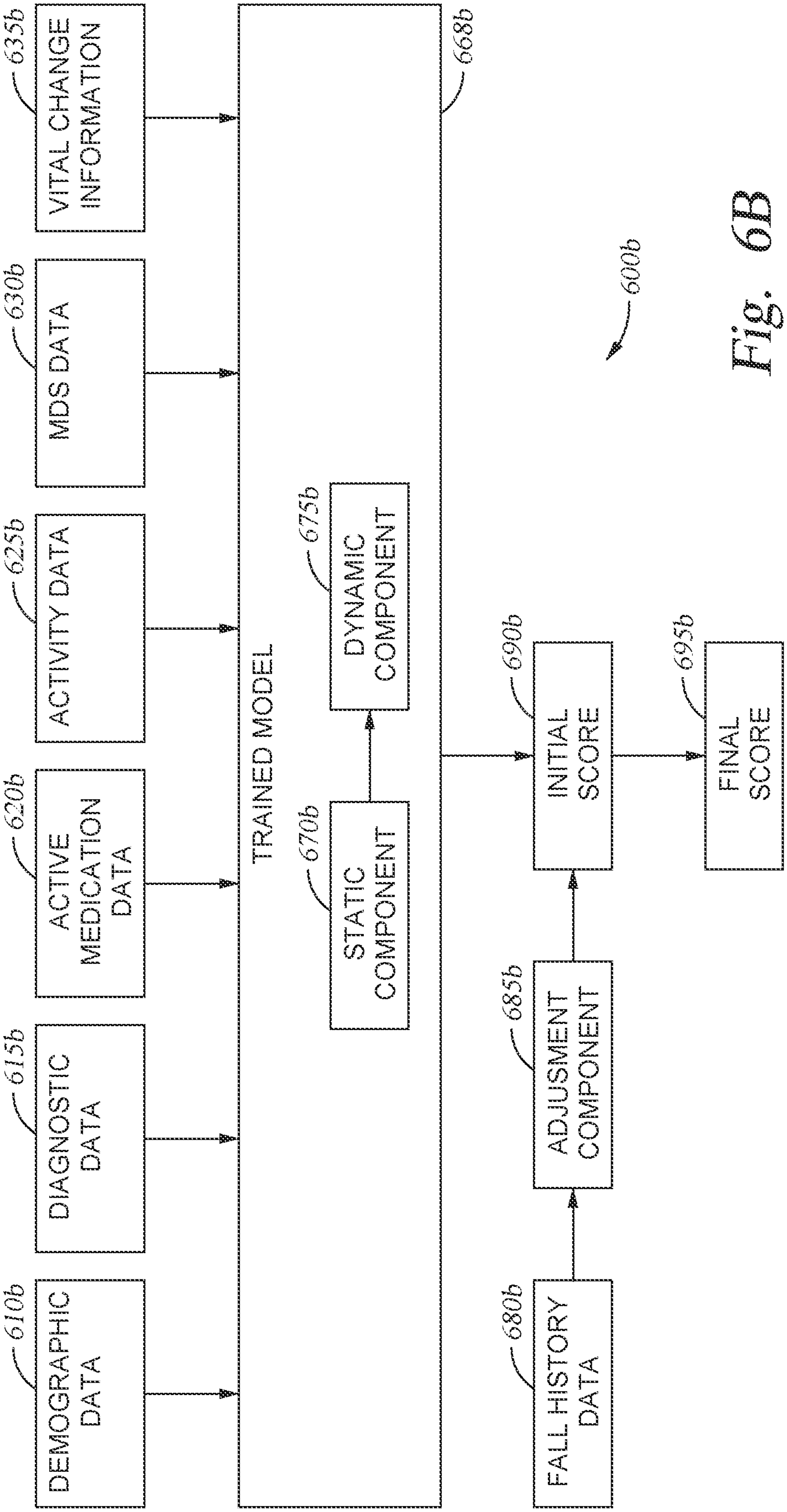
FIG. 6B is a machine learning architecture for predicting a fall, according to one or more implementations of the present disclosure.

FIG. 6B illustrates an architecture of an algorithm 600*b*, e.g. a trained algorithm with one or more machine learning components, that predict whether or not an individual will sustain a fall. In one or more implementations, the architecture includes any suitable software and/or hardware units necessary to carry out the logic and/or flow of operations of the architecture 600*b*. In one or more implementations, the architecture 600*b* is the basis for a fall risk algorithm and can be stored in a memory of an overall computer system and can be implemented by one or more computer processors. In one or more implementations, any other suitable system or component described herein can be configured to execute algorithm 600*b*. In one or more implementations, various components of algorithm 600*b* receive data associated with one or more individuals, e.g. demographic data 610*b*, diagnostic data 615*b*, medication data 620*b*, including active medication data, activity data 625*b*, Minimum Data Set (MDS) data 630*b*, and vital change information data 635*b*, where data 610*b*, 615*b*, 620*b*, 630*b*, and 635*b* can be as described above with reference to other implementations, where the data can be related to one or more individuals N (e.g. nursing home facility patients, hospital patients, etc.) as referenced with respect to other implementation as described above, and where the data sources can further be based in whole or in part on predetermined forms as described herein.

In one or more implementations, the algorithm 600*b* includes a trained model 668*b* and can be any suitable machine learning model, including but not limited to a static model, dynamic model, hybrid model, or any other suitable machine learning model.

In one or more implementations, as shown trained model 668 includes a dynamic component 675*b* in the form of a neural network and one or more static components 670*b*. In one or more implementations, the one or more static components 670*b* process data from one or more data sources 610*b*-635*b* and provide an output to the dynamic component 675*b*. In one or more implementations, the static components 670*b* include the static dictionaries developed with respect to FIG. 6A and are configured to apply a matching operation with respect to incoming data that matches entries in the static dictionary, e.g. medical or diagnostic data associated with 615*b* and/or 620*b*, that is of the same type as an entry in the static dictionaries developed with respect to FIG. 6A; and thereafter, the corresponding weight or weight averages associated with that data entry is inputted in the dynamic components (e.g. neural network) 675*b*.

In one or more implementations, the one or more static component 670*b* perform real time calculations, and include predetermined equations based on the ratio of individual diagnosis/medication that contributed to a fall event, subtracted by a ratio of individual diagnosis/medication contributed for a not fall event. In one or more implementations, one or more static components 670*b* are based on Equation 2 as provided for above. In one or more implementations, one or more static components 670*b* process one or more of the incoming data sources, generate a relational matrix and/or table with respect to the incoming data stream, and generate one or more weights with each data type in relation to a fall event. In one or more implementations, the one or more static components 670*b* generate an average of weights with respect to each data type and outputs the average into the dynamic model 675*b*.

In one or more implementations, the one or more static components 670*b* only process data from data sources 615*b* and 620*b* and the remaining data sources, e.g. 610*b*, 625*b*, etc. feed directly into the neural network 675*b*, and the overall model 668 produces one or more initial scores 690*b*, where the one or more initial scores 690*b* relate as to whether or not an individual will sustain a fall.

In one or more implementations, the one or more initial scores 690*a*, are adjusted by an adjustment component 685*b*. In one or more implementations, the adjustment component 685*b* can be a static component, where the static component 685*b* is a predetermined equation or factor that adjusts the score outputted by machine learning model 668. In one or more implementations, one of the most important indicators as to whether or not an individual will fall in the future is whether that individual has fallen in the past and the duration since the last fall. As such, in one or more implementations, the adjustment component 685*b* received fall history data 680*b*, e.g. based on a fall history of one or more individuals, and applies and equation, e.g. Equation 3 as provided above, to the initial score 690*a* to determine or generate a final score 695*a* as to whether or not an individual will likely suffer a fall. In one or more implementations, the adjustment component utilizes an equation that multiplies the number of days Nd since the last time an individual fell by a predetermined percentage factor, where the percentage factor can be determined by applying probabilistic and deviation techniques on data associated with the falls of other individuals. In one or more implementations, an equation in conjunction with thresholding operations. In one or more implementations, a processor can be configured to receive data and execute the operations indicated above with respect to the trained machine learning model 668.

In one or more implementations, as discussed and implied above, the use of a hybrid model with static and dynamic components in an overall algorithm, e.g. algorithm 600*b*, increases the accuracy of the overall algorithm, which is an overall improvement to a system, the prediction system 100 that employs the algorithm. Since certain factors that are identified with a higher statistical probability or significance with respect to whether or not an individual will fall, and since other factors that are identified of having a more variable nature in relation to a prediction, e.g. their relevance is more dependent on an overall profile of an individual, an algorithm that employs static weights for the former and dynamic or variable weights for the latter can produce a more accurate and efficient prediction as to whether or not an individual will fall. In one or more implementations, the use of an adjustment factor that is static and based on data determined to be of particular significance, e.g. previous fall history, the application of a factor based on such data, whether alone or in combination with a hybrid model (which increases accuracy by itself), can also increase the accuracy and efficiency of the output of the overall algorithm. Moreover, as stated and implied above, in one or more implementations, the use of both an adjustment factor and a hybrid machine model in an overall algorithm can have a compounding effect as to the accuracy of a score. Finally, since the total score associated with system can be based in whole or in part on the prediction score produced by algorithm 600*b*, the algorithm 600*b* can enhance the prophylactic effect of allocating resources to individuals likely to fall in accordance with the implementations of the present disclosure.

In one or more implementations, as stated and implied herein, the data that can be used to train the machine learning algorithm and the data used for application of the trained algorithm to make a prediction can be based on predetermined forms with a score or value range associated therewith, including with respect to the operations associated with FIGS. 6A and 6B.

Figure 6C:
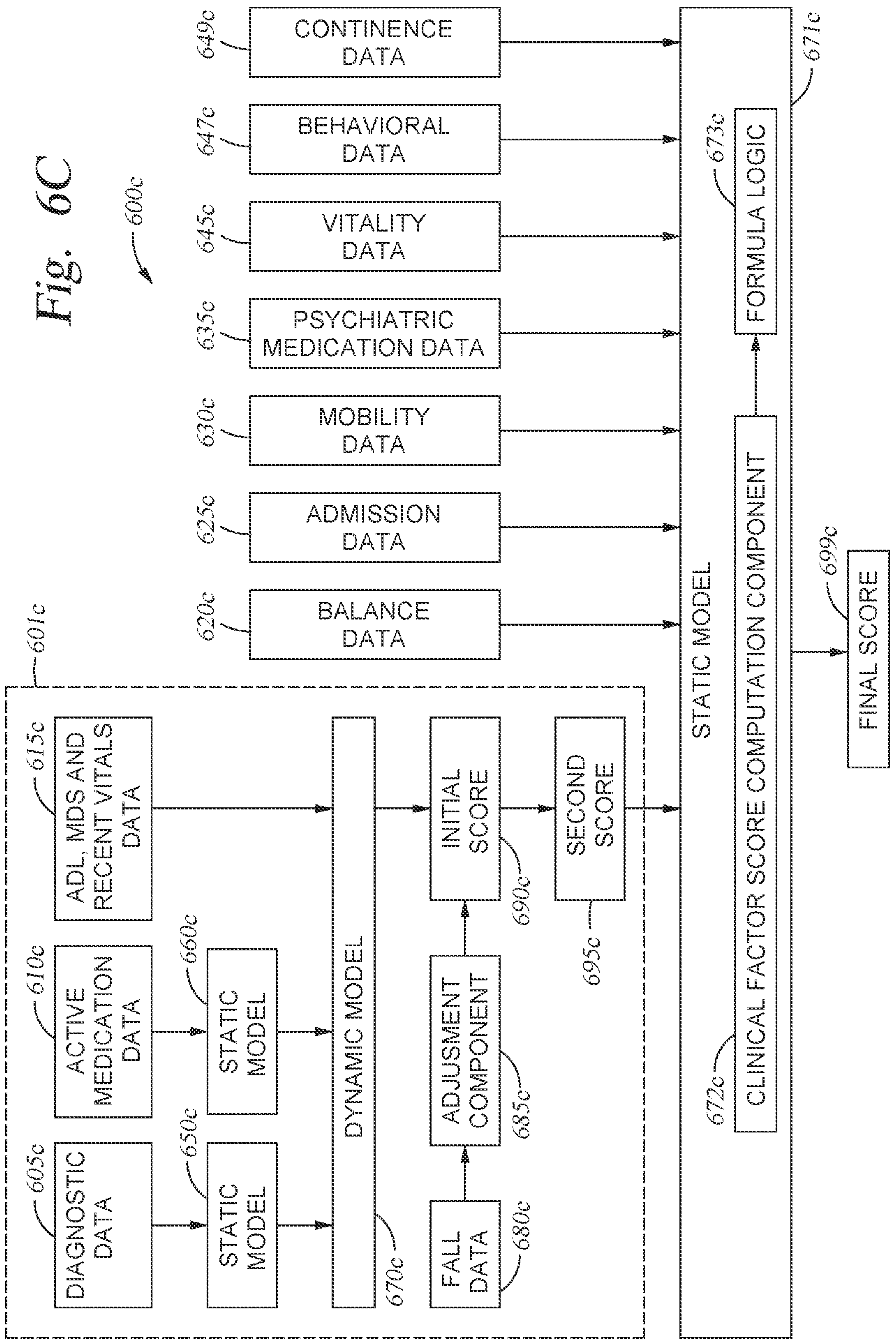
FIG. 6C is a machine learning architecture for predicting a fall, according to one or more implementations of the present disclosure.

Beginning in June of 2020, Applicant conducted confidential experiments with multiple healthcare/nursing-home facilities to determine the utility, accuracy, deploy-ability, and suitability of prototype systems and methods that predict a fall. As a result of these confidential activities and further development, additional techniques, systems, features and methods were discovered that further enhance an accuracy of a system or method to determine a fall, in addition to increasing the operability and efficiency of the same in application. FIGS. 6A-6C disclosed below, in addition to other embodiments or implementations disclosed herein, reflect some of these additional techniques, systems, features and methods.

FIG. 6C illustrates an architecture of an algorithm 600*c*, e.g. a trained algorithm with one or more machine learning components, that predict whether or not an individual will sustain a fall. In one or more implementations, the architecture includes any suitable software and/or hardware units necessary to carry out the logic and/or flow of operations of the architecture 600*c*. In one or more implementations, the architecture 600*c* is the basis for a fall risk algorithm and can be stored in a memory of an overall computer system, such as memory of a computer system, and can be implemented by one or more computer processors. In one or more implementations, any other suitable system or component described herein can be configured to execute algorithm 600*c*. In one or more implementations, various components of algorithm 600*c* receive data associated with one or more individuals, e.g. diagnostic data 605*c*, active and new medication data 610*c*, Activities of Daily Living (ADL), MDS, and Recent Vitals data 615*c*, balance data 620*c*, admission data 625*c* (e.g. admission to a hospital, care facility within a specified time frame, e.g. 24-48 hours), mobility data 630*c* (e.g. if a wheel chair, mechanical lift, or other assistance is required), psychiatric medication data 635*c* (e.g. where in one or more implementations, as discussed below, this can be a separate data category from active medication data 610*c*), vitality data 645*c*, behavioral data 647*c* (e.g. evidence of specific erratic behavior such as shaking), and continence data 649*c* (e.g. changes in continence), and fall history data 680*c*, where data 615*c*-649*c* and 680*c* can be as described above with reference to other implementations, where the data can be related to one or more individuals N (e.g. nursing home facility patients, hospital patients, etc.) as referenced with respect to other implementation as described above, and where the data sources can further be based in whole or in part on predetermined forms as described herein.

In one or more implementations, algorithm 600*c* includes component 601*c*, which in turn include static model 650*c*, static model 660*c*, dynamic model 670*c* and adjustment component 685*c*. Component 601*c* functions the same or substantially the same as described above with the various components described with respect to 600*a* and 600*b*, including training a neural network, e.g. 670*c*, developing and applying static dictionaries using static models, e.g. 650*c* and 660*c*, generating an initial score 690*c* based on the processing of the dynamic and static models, e.g. 650*c*,

660*c*, and 670*c*, adjusting the initial score 690*c* using an adjustment component 685*c* that receives fall history data 680*c* as an input to produce a second score 695*c*. In one or more implementations, unlike implementations with respect to FIG. 6A and FIG. 6B, the final score of 600*c* is based on additional processing and computations resultant from model 671*c* to generate final score 699*c*. In one or more implementations, the data source associated with component 601*c* can be in whole or in part as shown with respect to FIG. 6A and FIG. 6B, where in other implementations, as shown, the data ingested by the various components of 601*c* is more limited, e.g. 605*c*, 610*c*, and 615*c*, where the other data sources are processed by model 671*c*. In one or more implementations, since data sources 605*c*, 610*c*, and 615*c* can be considered a first plurality of data because said sources are associated with 601*c*, and data sources 620*c*-649*c* can be considered a second plurality of data associated with model 671*c*, where the data sources can actually be from a single source or multiple sources, with overlap as to the origin. In one or more implementations, data sources 620*c*-649*c* are specific clinical sources with data that is specific to individuals where a fall prediction is sought, where the data sources can be associated with predetermined weights (as discussed below), and where, with respect to model 671*c*, no training occurs except as to the determination and application of the predetermined weights.

In one or more implementations, as stated above and implied herein, experimentation and testing at one or more facilities has determined that utilizing an additional model, e.g. 671*c*, with specific data sources, e.g. real time data, that is specific to a particular individual or individuals can further generate a more accurate and tailored fall prediction score, which in turn can be used to provide a more appropriate prophylactic measure for one or more users. In one or more implementations, model 671*c* is a static model or series of static models determined by computational component or unit 672*c* and formula logic 673*c*. In one or more implementations, formula logic 673*c* applies one or more of a probabilistic, correlation, or other technique as discussed herein in relation to data sources 620*c*-649*c* such that data sources with the highest correlation to a fall receive a higher predetermined weight than other sources. In one or more implementations, the type of data that is most important with respect as to whether or not an individual will suffer a fall can be determined by a user through experimentation and/or by applying a correlation and/or probabilistic function to each individual data and determine which data types correlate the highest as to whether or not an individual suffers a fall. In one or more implementations, once the data sources are determined in terms of correlative value, formula logic 673*c* determines a weight associated with each data source, where the weights can be based in whole or in part on any suitable function, including iteratively increasing the weight value based on a specific factor or doing so partially with one iterative factor with respect to some data sources and another with respect to other data sources. For example, if it is determined that a change or lack thereof in behavior is the least important, and the next important is a continence change, then the weight, e.g., Wc, for continence change can be Wb (the weight for behavioral changes) plus a factor N, and where the next important data source, e.g. nutritional changes (e.g. lack of eating) can be Wc+N. In order to optimize accuracy, "N" can be constant between some data sources, but can change if a data source is particularly important, e.g. the weight for a data source can be Wp+N+N2, where Wp is the weight for the data source immediately precedent in importance, and N2 is an additional additive to the value. In one or more implementations, factorial increases, e.g. N, 2N, 3N, etc. can be used in whole or in part. In one or more implementations, the determination of which data category receives a particular weight value can be based on data associated with other individuals that have sustained a fall, where the data used to make that determination can be of the same type as 620*c*-649*c*. In one or more implementations, once the weights are determined, the computational component 672*c* can generate a clinical score by a summation of the weights for a particular individual, e.g. using the following Equation 4:

Clinical Score=$W1$*(balance change)+$W2$*(admitted in the last 24 hours)+$W3$*(assistance required in the last 24 hours)+$W4$*(psychotropic medication)+$W5$*(nutrition)+$W6$*(evidence of pain)+$W7$*(vitals out of range)+$W8$*(behavior changes)+$W9$*(continence change) . . . other factors.

The individual data categories, e.g. balance change, can be a "1" or "0" if a change in the particular category is detected or it can be a number based on threshold equations, e.g. as discussed above in reference to predetermined forms, where the initial number can be higher than one, e.g. where a particular medication is of a certain potency, a psychotic condition is of a more significant severity, etc. In one or more implementations, once the Clinical Score is determined, the formula logic 673*c* can apply a comparative scheme to determine what the scheme will be used to compute a final score. If the both the Clinical Score produced by the computational component 672*c* and the second score or fall risk model score 695*c* produced by component 601*c* both exceed a certain threshold or value T, e.g. 50, then the following scheme is applied to generate final score 699*c* (e.g. by the computational component 672*c*) using Equation 5:

Final Score=(Greater of Two Scores [i.e. Clinical and Second Score]+(Lesser of Two Scores [i.e. Clinical and Second Scores]*reducing scaling factor))/second scaling factor The greater of the two scores is added to the lesser of the two scores adjusted by a scaling factor, where the lesser of the two scores is multiplied by any suitable factor to reduce its value (e.g. based on a product, difference or a product and difference, etc.), and where the sum is divided by another scaling factor.

If the two scores are below the certain threshold T, and are within a certain range R1, e.g. the difference is small, then the final score 699*c* is the higher of the two scores (e.g. where the computation is performed by the computational component 672*c*).

If the two scores are beneath the certain threshold T, but the difference is greater than R1, then the final score 699*c* is an average of the scores (e.g. where the computation is performed by the computational component 672*c*).

In one or more implementations, since the algorithmic features of component 601*c* include both a score based on a fall prediction stemming from whether previous falls have occurred and what the likelihood is that a fall will occur as a result therefrom, e.g. second score 695*c*, and a clinical factor score produced by computation unit 672*c* that is based on a scheme that accounts for clinical factors unique to the subject for which a score is to be determined, a more accurate result is generated, where said accurate result can be used to provide a superior prophylactic measure in relation to a potential fall for a patient or resident of a care facility or hospital.

In one or more implementations, as stated and implied herein, the data associated with FIG. 6C can also be based on predetermined forms to enhance accuracy and efficiency in relation to said score.

Figure 7A:
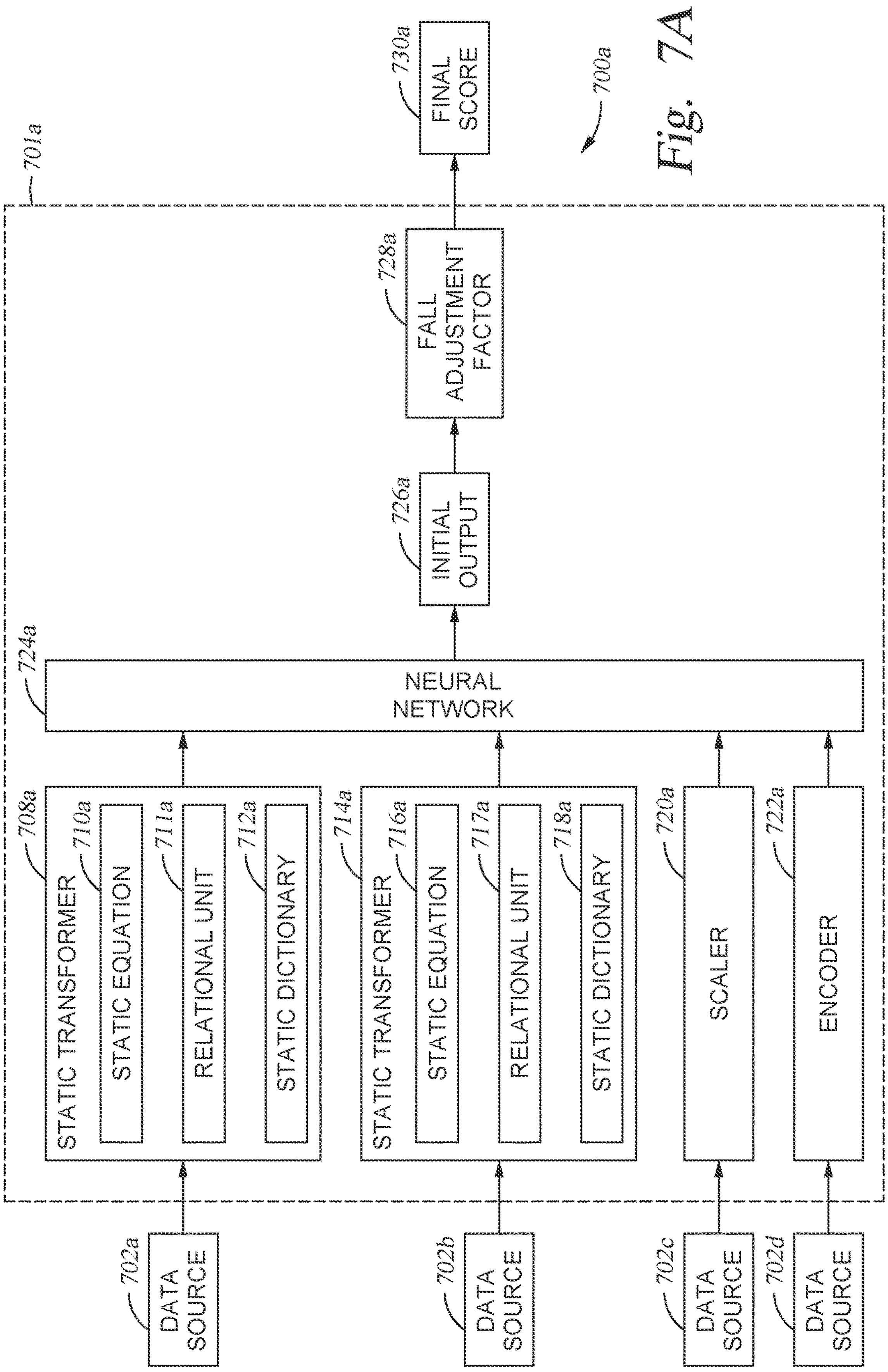
FIG. 7A is a machine learning training architecture, according to one or more implementations of the present disclosure.

FIG. 7A illustrates an architecture 700*a* for training a machine learning algorithm according to one or more implementations of the present disclosure. In one or more implementations, the architecture includes any suitable software and/or hardware units necessary to carry out the logic and/or flow of operations of the architecture 700*a*. In one or more implementations, architecture 700*a* can form the basis for training fall risk algorithm and can be stored in a memory of an overall computer system and can be implemented by one or more computer processors. In one or more implementations, any other suitable system or component described herein can be configured to execute the architecture (e.g. as an algorithm) of 700*a*.

In one or more implementations, algorithmic architecture 700*a* includes a computational unit 701B, which further includes a static transformer 708A, a static transformer 714A, a scaler 620A, an encoder 722A, a neural network 724A, and a fall adjustment component 728A. In one or more implementations, static transformers 708A, 714A include one or more static operations 710A, 716A, where static operations 710, 716A can include one or more operations based on Equation 2. In one or more implementations, static transformers 708A, 714A intake data from data sources 702A, 702B, respectively. In one or more implementations, the architecture 700*a* includes a pre-processing unit for performing pre-processing operations to data associated with one or more data sources.

In one or more implementations, data source 702A is data related to medical diagnoses associated with one or more individuals. In one or more implementations, data source 702B is data related to medication information, e.g. active medication, associated with one or more individuals. In one or more implementations, the medical and diagnostic data can be collected for a specified time period, e.g. for fourteen days prior with respect to each of the one or more individuals associated with the data. In one or more implementations, a user (as shown with reference to other implementations) can enter data into the data sources (e.g. databases) associated with 702A and 702B within the specified time range and in one or more implementations, a pre-processing unit can perform a filtering operation, e.g. filter out all data outside the time range (e.g. within fourteen days).

In one or more implementations, static transformers 708A, 714A include relational units 711A, 717A, respectively, where relational units 711A, 717A generate tables associating fall and non-fall events in relation to the respective data sources feeding static transformers 708A, 714A. In one or more implementations, static operations 710A, 716A intake the data from their respective data sources, apply Equation 2, and in coordinating with the relational units 711A, 717A, respectively, generate tables with static weights associated with each row of a table, and in relation to a particular data entry; thereafter, the average of the weights of each instance are utilized by the static transformers 708A, 714A to be used in training neural network 724A. An example of these operations can be as follows: a portion of diagnostic data can be categorized into the following Table 1, which includes ICD codes:

TABLE 1

| Id | Diagnosis | Event |
|---|---|---|
| 1 | Z96.642, N39.0, R52, I10, F32.9, E78.5, N39.0, R25.1 | Fall |
| 2 | K56.699, N39.0, K59.00, K21.9, R52 | Not Fall |
| 3 | N39.0, R52, I10, F32.9, E78.5 | Fall |

In one or more implementations, with respect to diagnostic data 702A, the diagnostic data source 702A can include fall information for one or more individuals and/or another data source (as shown with reference to other implementations) can contain the fall or not fall information. In one or more implementations, the relational unit 711A generates one or more rows (e.g., historical records like as shown in FIG. 4 with sequences of entries (e.g., multiple data entries) of ICD codes "Z96.642," "N39.0, R52," "I10, F32.9," etc. where each particular row of data, as shown, is a representation of diagnostic information for a particular patient. In one or more implementations, as stated and implied above, the relational unit 711A can form this relational table or matrix. In one or more implementations, the static operations 710A can be applied as follows by using the method 500 in FIG. 5, with specific example being with respect to "N39.0" (i.e., the selected entry of the sequence of entries): N39.0 appears two times in the Fall entry and the Id 1, and the sequence contains 8 diagnosis, the row weight for N39.0 is 2/8=0.25 for Fall; N39.0 appears one time in the Not Fall entry and the Id 2, and the sequence contains 5 diagnosis, the row weight for N39.0 is 1/5=0.2 for Not Fall; N39.0 appears one times in the Fall entry and the Id 3, and the sequence contains 5 diagnosis, the row weight for N39.0 is 1/5=0.2 for Fall; and where the sum up of row weights for N39.0 on Fall entries resolves as follows: (0.25+0.2)=0.45, and with the same for Not Fall being 0.2. With the initial weights computed, application of Equation 2 for a subsequent weight result is as follows: (0.45/0.2)−(0.2/045)=1.80556. Accordingly, the static weight for N39.0 is 1.80556. This weight can then be stored in a static model dictionary (e.g., the dictionary 300 in FIG. 3). (It is noted that in one or more implementations, the calculation sign can also determine whether the particular diagnosis leans towards Fall or Not Fall, e.g. if the sign is negative, then it is leaning towards Not Fall, e.g. if the sign is positive, it is leaning towards Fall, e.g. if the weight is 0 then it is neutral). Thereafter, a weight for each of the ICD codes in Table 1 can be calculated using the above process and saved as a static model dictionary, e.g. static model dictionary 712A, which can be used in training the neural network 724A as discussed in the method 200 in FIG. 2. In one or more implementations, prior to initializing training, each sequence will be transformed by replacing weights based on the static model dictionary and the average of it is used in training the neural network 724A. For example, Z96.642, N39.0, R52, I10 will be transformed as follows: (0.1+1.80556+(−0.23)+0.2)/4=0.46889. In one or more implementations, the same process of operations and static dictionary formation can be used by static operations 716A and relational unit 717A to construct static dictionary 718A with respect to medical data provided by data source 702B. In various implementations, a static dictionary can be formed utilizing a combination of data from 702A and 702B and utilizing the above operations. Moreover, the weights in the static dictionary can also be used to make a prediction using a trained ML model as discussed in FIG. 2.

In one or more implementations, as shown, the architecture 700*a* includes data source 702C and 702D, where data source 702C includes MDS information, ADL information, demographic information, and age information of one or more individuals. In one or more implementations, the MDS information can be filtered (e.g. by the pre-processing unit) based on a temporal quality, e.g. only MDS information within a certain time frame is collected. In one or more implementations, MDS information can contain ordinal scale and natural ranking (by virtue of its nature), and can be of an integer nature, which can further enhance an accuracy and efficiency of a model being trained utilizing such information, as pre-processing and natural language processing operations can be minimized before and after the training process in relation therewith. In one or more implementations, where the data source 702C is in whole or in part based on information from medical, nursing home, or assisted care facilities, the value of the data sources 702C can be set as follows by the pre-processing unit: if a resident is refused, −99 is used as a value; if the value is null, −1 is can be used as a value; and if the value is unknown, −2 can be used as value; where in one or more implementations, applying this categorization to the data enhances the efficiency of the training process and/or increases the accuracy of a machine learning model to be trained by this data, e.g. neural network 724A, by ensuring all relevant data can be processed and processed in an efficiently recognizable form (e.g. integer nature).

In one or more implementations, the ADL data of data source 702C can also be restricted to a particular temporal range, e.g. within 14 days, where the pre-processing unit 603C can filter out data outside this range prior to initiating model training, and where the assist categories associated are within a 14 day time period. In one or more implementations, repeated entries for a particular assist category of the ADL data, e.g. on a particular day, can be considered as a count "1" for a particular day, with missing values being replaced with "0."

In one or more implementations, data source 702C can include information related to the vitals of one or more individuals. In one or more implementations, the vital information is filtered by the pre-processing unit 603C and/or pre-set by a user to be with an average deviation of the last three entries for each one of the one or more individuals, with missing values being replaced with a "0."

In one or more implementations, data source 702D can include information related to the demographics and age of an individual. In one or more implementations, when an age or gender of an individual is unknown, the value associated therewith is set by the pre-processing unit and/or a user to "0" or "UNKNOWN."

In one or more implementations, all of the data of data source 702C, after pre-processing by a user and/or pre-processing unit, can be inputted into a suitable scaler, e.g. 720A, for more efficient processing in relation to training neural network 724A. For example, a min/max scaler (0, 1) can be applied to further enhance the processing speed of training the neural network 724A, and ultimately improve the accuracy of the trained neural network 724A. Similarly, in one or more implementations, an encoding scheme or encoder, e.g. 722A, such as One Hot Encoding, can be applied to the gender and demographic data associated with data source 702D to achieve the same aim.

In one or more implementations, the outputs of the static transformer 708*a*, static transformer 714*a*, scaler 720A, and encoder 722A are inputted into the neural network 724A. Any suitable technique as discussed herein, e.g. deep learning techniques (e.g. backpropagation, etc.) can be used to train the neural network with the received inputs. In one or more implementation, neural network 724A can be initialized with calculated bias and class weights. In one or more implementations, the neural network 724A can be trained with 100 EPOCHs and a batch size of 512. In one or more implementations, the neural network 724A can be trained offline or online. In one or more implementations, the neural network 724A can be trained offline with a sample size of approximately 2 million, an accuracy of 0.86 and F1-score of 0.86 on the out of sample(unseen) dataset(s) (as associated with each of the relevant data sources).

In one or more implementations, the computational unit 701*b* includes a fall adjustment component 728A. In one or more implementations, the fall adjustment component 728A receives data from data source 702E, where data source 702E includes fall history information associated with the one or more individuals associated with data sources 702A-702D. In one or more implementations, the fall adjustment component receives data related to fall history from other data sources, e.g. in implementations where the fall history of the one or more individuals is contained in one or more of data sources 702A-702D. In one or more implementations, the fall adjustment component 728A applies Equation 3 to fall history information associated with the one or more individuals and applies the output of Equation 3 to an initial score or output 726A generated by the neural network 724A to generate a final score 730A related to whether or not an individual will sustain a fall. In one or more implementations, the adjustment component 728A applies one or more additional thresholding operations and computational operations to generate the adjustment factor. For example, one or more threshold operations can be applied to an initial score to determine what type of adjustment factor will be applied to the initial fall prediction. For example, in one or more implementations, the one or more threshold operations can be related to the value of the initial score, the number of falls associated with a particular individual, and/or the time frame associated with those falls. By way of a specific example, and according to one or more implementations, the application and operations of the adjustment factor or protocol can be as follows: If a fall event is within 30 days and an initial score is less than 90%, then the final score can be adjusted as follows: 90+(0.2*Nf on prior 30 days). If a fall event is within 30-90 days and the initial score is less than 80%, then 80+(0.2*Nf on prior 30-90 days). If a fall event is within 90-365 days and an initial score is less than 70%, then 70+(0.2*Nf counts on prior 90-365 days).

In one or more implementations, the training of neural network 724A incorporates the results of the adjustment component 728A (e.g. during application of deep learning techniques), and in one or more implementations the results of the adjustment component are not used.

Figure 7B:
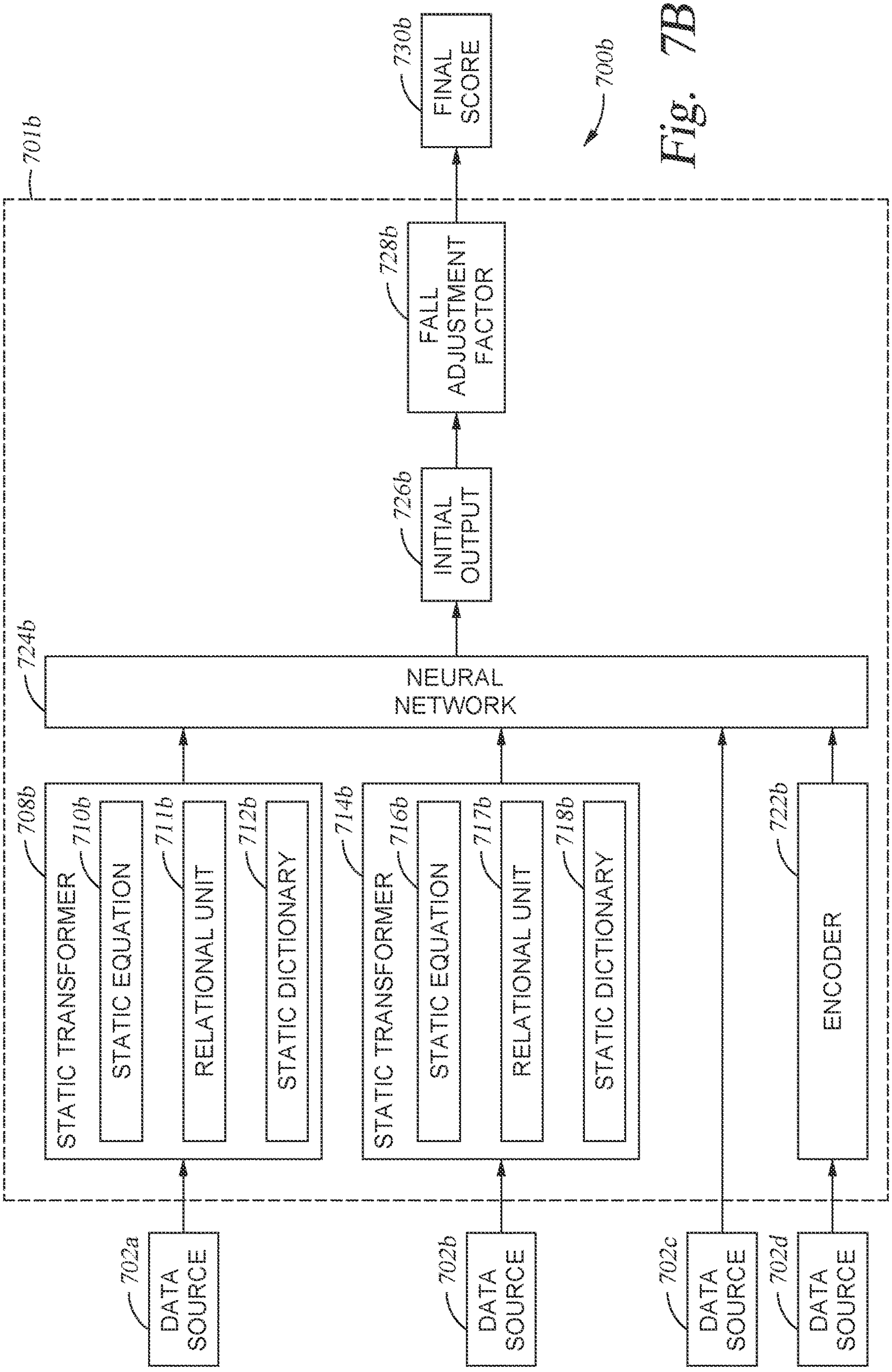
FIG. 7B is a machine learning architecture for predicting a fall, according to one or more implementations of the present disclosure.

FIG. 7B illustrates an architecture 700B for applying a (trained) algorithm to predict whether one or more individuals will suffer a fall according to one or more implementations of the present disclosure. In one or more implementations, the architecture includes any suitable software and/or hardware units necessary to carry out the logic and/or flow of operations of the architecture 700*b*. In one or more implementations, the architecture can form the basis for one or more, or all of the operations associated with machine learning training protocol algorithm 408*a*. In one or more implementations, the architecture 700*b* can serve as the logical or operational architecture for machine learning application component 408*b*. In one or more implementations, architecture 700*b* can form the basis for training fall risk algorithm 118 and can be stored in a memory of an overall computer system, such as memory 144 of computer system 100, and can be implemented by one or more computer processors, such as processor 142 of computer system 100. In one or more implementations, any other suitable system or component described herein can be configured to execute the architecture (e.g. as an algorithm) of 700*b*.

In one or more implementations, algorithmic architecture 700*b* includes a computational unit 701*b*, which further includes a static transformer 708B, a static transformer 714B, a neural network 724B, and a fall adjustment component 728B. In one or more implementations, computational unit 701*b* includes one or more components trained and/or determined by architecture 700A; for example, a trained neural network 724B stemming from the training of training neural network 724B and static dictionaries 712B, 718B (stemming from 712A, 718A, respectively). In one or more implementations, static transformers 708B, 714B include one or more static operations 710B, 716B, where static operations 710B, 716B can include one or more operations based on Equation 2. In one or more implementations, static transformers 708B, 714B intake data from data sources 702A', 702B', respectively.

In one or more implementations, data source 702A' is data related to medical diagnoses associated with one or more individuals. In one or more implementations, data source 702B' is data related to medication information, e.g. active medication, associated with one or more individuals. In one or more implementations, the data sources 702A' and 702B' are data sources associated with distinct individuals than the individuals associated with the data sources of training, e.g. with the one or more individuals associated with architecture 700A. In one or more implementations, the data of architecture 700A overlaps with the data of architecture 700B. In one or more implementations, no pre-processing of data occurs with respect to 702A' and 702B'. In one or more implementations, a pre-processing occurs as with respect to FIG. 7A, e.g. the medical and diagnostic data can be collected for a specified time period, e.g. for fourteen days prior with respect to each of the one or more individuals associated with the data. In one or more implementations, a user (as shown with reference to other implementations) can enter data into the data sources (e.g. databases) associated with 702A and 702B within the specified time range and in one or more implementations, a pre-processing unit (as shown with reference to other implementations) can perform a filtering operation, e.g. filter out all data outside the time range (e.g. within fourteen days).

In one or more implementations, the static transformer 708B, 714B are the static transformers 708A, 714A and the dictionaries 712B and 718B are the dictionaries 712A and 718B, respectively, developed as outlined with respect to FIG. 7A. In one or more implementations, static transformer 708A and 714A intake data from data sources 702A' and 702B' and perform a matching operation utilizing units 712B and 718B, respectively. In one or more implementation, the matching units 711B and 717B match a data in static dictionaries 712B and 718B, respectively, to data from an incoming data stream associated with one or more individuals. For example, if an individual has a diagnosis type and/or takes a medication that is of the same type as an entry of the one or more static dictionaries 712B, 718B, then the relevant matching unit will output the one or more weights and/or weight averages associated with the relevant static dictionary entry from the static model dictionary (e.g., the dictionary 300 in FIG. 3) into the neural network 724B. In one or more implementations, no computation associated with static operations 710B and 716B when matching is performed, e.g. the weights and weight averages from the development/training of static dictionaries from training (e.g. as discussed with respect to FIG. 7A) are used.

In one or more implementations, static transformers 708B, 714B include relational units 711B, 717B, respectively, where relational units 711A, 717A generate tables associating fall and non-fall events in relation to the respective data sources feeding static transformers 708A, 714A. In one or more implementations, static operations 710A, 716A intake the data from their respective data sources, apply Equation 2, and in coordinating with the relational units 711A, 717A, respectively, generate tables with static weights associated with each row of a table, and in relation to a particular data entry; thereafter, the average of the weights of each instance are utilized by the static transformers 708A, 714A to be used as inputs in the neural network 724B. Accordingly, in one or more implementations, the static dictionaries 712B, 718B include new or updated entries from the static dictionaries from training, and/or replace those entries in their entirety.

In one or more implementations, as shown, the architecture 700B includes data source 702C' and 702D', where data source 702C' includes MDS information, ADL information, demographic information, and age information of one or more individuals. In one or more implementations, no filtering or pre-processing of the information occurs.

In one or more implementations, the MDS information can be filtered (e.g. by the pre-processing unit (as shown with reference to other implementations)) based on a temporal quality, e.g. only MDS information within a certain time frame is collected. In one or more implementations, MDS information can contain ordinal scale and natural ranking (by virtue of its nature), and can be of an integer nature, which can further enhance an accuracy and efficiency of a trained model being applied to incoming data. In one or more implementations, where the data source 702C' is in whole or in part based on information from medical, nursing home, or assisted care facilities, the value of the data sources 702C; can be set as follows by a pre-processing unit (as shown with reference to other implementations) or user: if a resident is refused, −99 is used as a value; if the value is null, −1 is can be used as a value; and if the value is unknown, −2 can be used as value; where in one or more implementations, applying this categorization to the data enhances the efficiency of the application process and/or increases the accuracy of a trained machine learning model to applied to this data, e.g. neural network 724B, by ensuring all relevant data can be processed and processed in an efficiently recognizable form (e.g. integer nature).

In one or more implementations, the ADL data of data source 702C' can also be fed into neural network 724B without preprocessing, where in one or more implementation it can also be restricted to a particular temporal range, e.g. within 14 days, where a pre-processing unit (as shown with reference to other implementations) can filter out data outside this range prior to initiating model training, and where the assist categories associated are within a 14 day time period. In one or more implementations, repeated entries for an assist category of the ADL data, e.g. on a particular day, can be considered as a count "1" for a particular day, with missing values being replaced with "0."

In one or more implementations, data source 702C' can include information related to the vitals of one or more individuals. In one or more implementations, the vital information is not filtered. In one or more implementations, the data can be filtered by a pre-processing unit (as shown with reference to other implementations) and/or pre-set by a user to be with an average deviation of the last three entries for each one of the one or more individuals, with missing values being replaced with a "0."

In one or more implementations, data source 702D' can include information related to the demographics and age of an individual. In one or more implementations, when an age or gender of an individual is unknown, the value associated therewith is set by a pre-processing unit (as shown with reference to other implementations) and/or a user to "0" or "UNKNOWN." In one or more implementations, no pre-processing is done.

In one or more implementations, all of the data of data source 702C' can be inputted directly into neural network 724B. In other implementations (as shown with reference to other implementations), the data of data source 702C' can be inputted into a suitable scaler for more efficient processing in relation to applying the neural network 724B to obtain a prediction as to whether or not one or more individuals will sustain a fall. For example, a min/max scaler (0, 1) can be applied, e.g. in instances where a significant number of predictions are requested. Similarly, in one or more implementations, an encoding scheme or encoder (as shown with reference to other implementations), such as One Hot Encoding, can be applied to the gender and demographic data associated with data source 702D' to achieve the same aim; and where in other implementations, no such encoding scheme is employed.

In one or more implementations, the outputs of the static transformer 708A and static transformer 714B, and data sources 702C and 702D are inputted into the neural network 724B in order to generate a prediction in relation to the one or more individuals where a prediction as to whether or not a fall will occur is sought. In one or more implementations, the neural network 724B generates an initial score 726B based on the inputted information, where the initial score 726B is an initial score indicative as to the likelihood than an individual (associated with data sources 702A'-702E') will sustain a fall.

In one or more implementations, the computational unit 701B includes a fall adjustment component 728B. In one or more implementations, the fall adjustment component 728B receives data from data source 702E', where data source 702E' includes fall history information associated with the one or more individuals associated with data sources 702A'-702D'. In one or more implementations, the fall adjustment component 728B receives data related to fall history from other data sources, e.g. in implementations where the fall history of the one or more individuals is contained in one or more of data sources 702A'-702D'. In one or more implementations, the fall adjustment component 728B applies Equation 3 to fall history information associated with the one or more individuals and applies the output of Equation 3 to an initial score or output 726B generated by the neural network 724B to generate a final score 730B related to whether or not an individual will sustain a fall. In one or more implementations, the adjustment component 728B applies one or more additional thresholding operations and computational operations to generate the adjustment factor. For example, one or more threshold operations can be applied to an initial score to determine what type of adjustment factor will be applied to the initial fall prediction. For example, in one or more implementations, the one or more threshold operations can be related to the value of the initial score, the number of falls associated with a particular individual, and/or the time frame associated with those falls. By way of a specific example, and according to one or more implementations, the application and operations of the adjustment factor or protocol can be as follows: If a fall event is within 30 days and an initial score is less than 90%, then the final score can be adjusted as follows: 90+(0.2*Nf on prior 30 days). If a fall event is within 30-90 days and the initial score is less than 80%, then 80+(0.2*Nf on prior 30-90 days). If a fall event is within 90-365 days and an initial score is less than 70%, then 70+(0.2*Nf counts on prior 90-365 days).

In one or more implementations, the final score 730B is outputted to a user that made a request (via a computing device accessing architecture 700B) for a prediction as to whether or not an individual (associated with data sources 702A'-702D') will suffer a fall.

Figure 8:
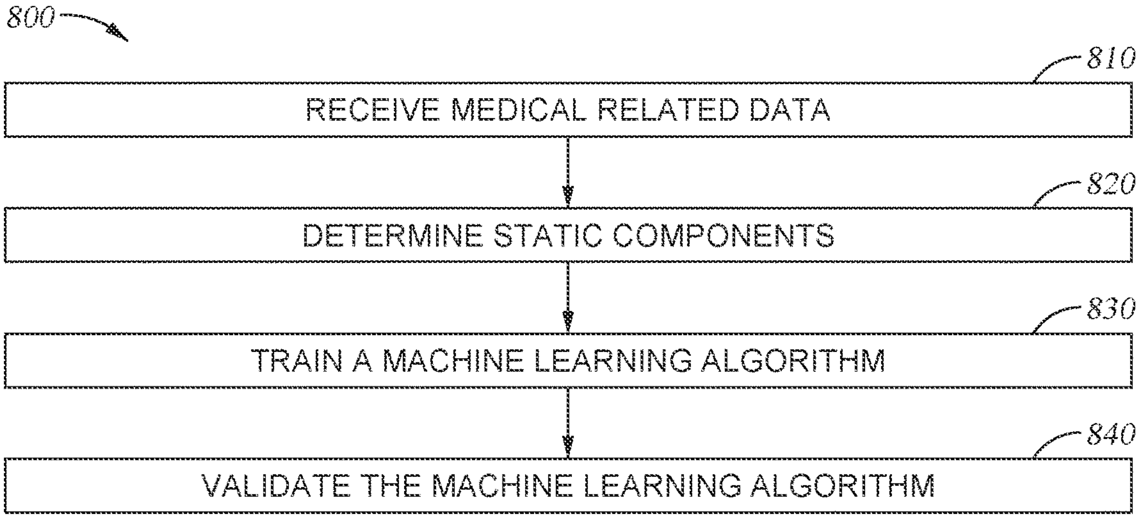
FIG. 8 is a process flow diagram for a method of training a machine learning mode, according to one or more implementations of the present disclosure.

FIG. 8 illustrates a flow 800 for training a machine learning model in accordance with various techniques associated with the present disclosure. In one or more implementations, the flow includes block 810, where any suitable computer system or component, e.g. system 100 and processors 114, receives a plurality of data, e.g. medical data, associated with a first set of one or more individuals. Here, receiving can mean inputting the data by any means such as keying, or data transfer from a data set (e.g., MDS, ADS, and electronic medical records). In one or more implementations, the received medical data includes: i) a demographic information associated with the one or more individuals, ii) a physical activity information associated the one or more individuals, iii) a vital change information associated with the one or more individuals, iv) governmental information associated with the one or more individuals, v) a medical diagnostic information associated with the one or more individuals, vi) medication information associated with the one or more individuals, vii) a demographic information associated with the one or more individuals, viii) a physical activity information associated with the one or more individuals, and ix) vital change information associated with the one or more individuals.

In one or more implementations, the flow 800 includes a block 820 for determining one or more static components of an overall algorithm for predicting a fall. In one or more implementations, the one or more static components can be predetermined by a user (e.g. via experimentation) and/or developed utilizing any other probabilistic, correlation, or other technique as discussed herein. In one or more implementations, the one or more static components can be based on particular types of data that are identified as the most important types of data in relation to whether or not an individual will sustain a fall. In one or more implementations, the type of data that is most important with respect as to whether or not an individual will suffer a fall can be determined by a user through experimentation and/or by applying a correlation and/or probabilistic function to each individual data and determine which data types correlate the highest as to whether or not an individual suffers a fall.

In one or more implementations, the data associated with the highest correlation as to whether or not an individual will suffer a fall, e.g. fall history, can be processed according to a first static model or equation or series of threshold operations in conjunction with an equation, e.g. Equation 3 and thresholding operations discussed above, and can serve as an adjustment factor during training. In one or more implementations, the next two most important data types, e.g. diagnostic data and active medication data, can be processed by one or more static models based on Equation 2 and one or more averaging operations, where the outputs of the static equations or models associated with Equation 2 can serve as an input for training a dynamic component, as discussed below. In one or more implementations, the suitable operations to generate the static models and other operations of block 820 can be performed by any suitable computer system and its associated components, e.g. the processor 142 of computer system 100 can be configured to determine the equation based on the received data utilizing any suitable technique as described herein.

In one or more implementations, flow 800 can include block 830 for training a machine learning algorithm based on the received data. Block 830 can include an initialization operation for setting initial weights for the machine learning model. The initial weights can be randomized or determined by probabilistic and deviation techniques from a test set of other individuals and similar data types in relation to those first plurality of individuals. Alternatively, the initial weights can be set to zero, can be set to a random value by application of a random weight generator, or can be provided by another machine learning model or system. In one or more implementations, the training can begin with a calculated bias and class weights pursuant to any other suitable initialization operation.

In one or more implementations, block 830 can include inputting the outputs of the determined static models based on Equation 2 and the remaining data sources not processed by the static models based on Equation 2, e.g. a demographic information associated with the one or more individuals, governmental information associated with the one or more individuals, etc. into a neural network, e.g. dynamic model. In one or more implementations, block 830 can include training the neural network utilizing any suitable training technique based on the received inputs discussed above, and can include modulating and adjusting weights and biases in the medical-related input data, and in deeper levels of a deep learning algorithm (e.g., by back propagation methods) such that the prediction of the fall score value is increasingly accurate. That is, a deviation from the fall score value and the prediction from the algorithm as it is trained is minimized to an acceptable minimum value. For example, at block 840 the model can be validated with a Root Mean Squared Error on train/test ratio 70:30 (i.e., 70% of the data is used to train the model and 30% of the data is used to test the model). In one or more implementations, the training is based solely on the received inputs from the static models based on Equation 2 and the other data sources. In one or more implementations, the training associated with block 830 can include incorporation of the static model based on Equation 3, e.g. a fall history adjustment factor, where, during training, an initial score is produced by the neural network, based on the inputs provided by the static models based on Equation 2 and the other data sources, and then a final score is produced by an adjustment factor based on fall history, where the backpropagation loop is from the output associated with the final score.

In one or more implementations, any iteration or run rate can be utilized, where in one or more implementations the neural network can be trained with one hundred EPOCHS and a BATCHSIZE set at 512. In one or more implementations, the model can be trained online or offline, where in one or more implementations the neural network was trained offline. In one or more implementation, any suitable data sample size based on block 810 can be used, where in one or more application a 2.3 million sample with an accuracy of 0.86 and F1-score of 0.86 on the out of sample(unseen) dataset can be used.

Accordingly, in one or more implementations the trained machine learning model is a hybrid model that includes both a static and dynamic aspect, e.g. static and variable weights, and the trained model can receive a second plurality of medical data associated with a second plurality of individuals and generate a prediction as to whether or not any one of those individuals will suffer a fall by outputting a score or value reflective of said prediction. In one or more implementations, the variable weights associated nodes can change and/or be updated with each application of the trained model.

Figure 9:
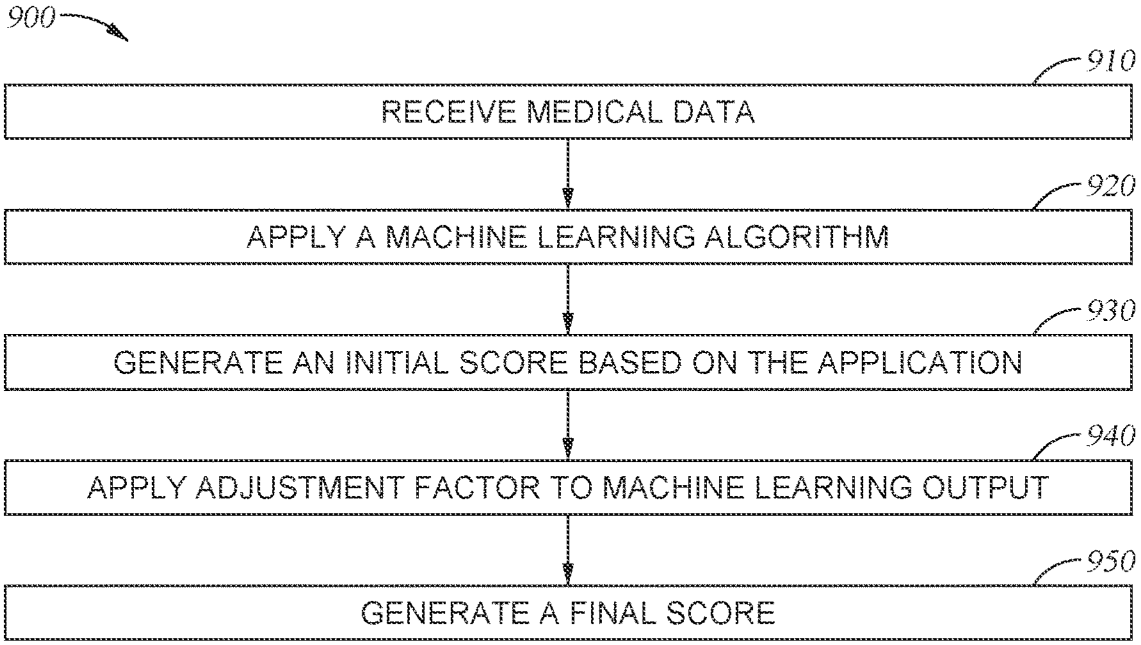
FIG. 9 is a process flow diagram for a method of utilizing a machine learning model, according to one or more implementations of the present disclosure.

FIG. 9 illustrates a flow diagram 900 for applying an algorithm to predict a fall of one or more individuals. In one or more implementations, the flow 900 includes block 810, where any suitable computer system or component, e.g. system 100 and processor 142, receives a plurality of data, e.g. medical data, associated with a first set of one or more individuals. Here, receiving can mean inputting the data by any means such as keying, or data transfer from a data set (e.g., MDS, ADS, and electronic medical records). In one or more implementations, the received medical data includes: i) a demographic information associated with the one or more individuals, ii) a physical activity information associated the one or more individuals, iii) a vital change information associated with the one or more individuals, iv) governmental information associated with the one or more individuals, v) a medical diagnostic information associated with the one or more individuals, vi) medication information associated with the one or more individuals, vii) a demographic information associated with the one or more individuals, viii) a physical activity information associated the one or more individuals, and ix) vital change information associated with the one or more individuals.

In one or more implementations, pursuant to block 920, any suitable component or components of a computer system can apply any machine learning algorithm or algorithm to the received data to generate an initial score, with respect to each of the one or more individuals associated with the received data, as to a potential fall event. For example, computer processor 142 can process the received data, e.g. 114, and can provide one or more instruction in relation to system 100, such as to apply algorithm 118 to the received data. Algorithm 118 can be a hybrid machine learning model that includes a neural network and one or more static models. In one or more implementations, the neural network directly receives a portion of the incoming data stream and another portion can be processed by one or more static models, including static models or dictionaries based on Equation 2. In one or more implementations, the static models utilize a static dictionary based on average weights that correspond to a particular type of data that is the same as the type of data received during training of the neural network. In one or more implementations, the application of the static portion of the algorithm involves performance of one or more matching operations that match incoming data to data in a static dictionary (e.g. generated during a training phase and based on Equation 2, an example of which is shown in FIG. 3), and output weight or weight averages associated with entries of the static dictionary into the neural network. This is discussed in more detail at block 245-255 of method 200. In one or more (other) implementations, the static models construct a table or matrix based on the incoming data stream, produce one or more static weights associated with fall or non-fall events, e.g. pursuant to Equation 2, and then average those weights to serve as an input to the neural network.

In one or more implementations, pursuant to block 920, all remaining data sources that are not processed by the static models are fed directly into the neural network.

In one or more implementations, pursuant to block 930, the application of the machine learning model, e.g. a hybrid machine learning model, can produce an initial score associated with each of the plurality of individuals, and where the score provides a prediction as to whether or not an individual will experience a fall event.

In one or more implementations, pursuant to block 940, any suitable component or components of a computer system can apply an adjustment factor to each of the initial scores produced for each one of the plurality of individuals. For example, computer processor 142 can process the received data, e.g. 114, and can provide one or more instruction in relation to system 100, such as to apply algorithm 118 to the received data. Algorithm 118 can include an equation as discussed herein that adjusts the output of the machine learning algorithm by either adding a factor to the initial score or performing a multiplication of the factor in relation to the initial output. In one or more implementations, the adjustment factor is based on Equation 2. In one or more implementations, the adjustment factor is based on Equation 3 and threshold operations as discussed herein.

In one or more implementations, pursuant to block 940 of flow 900, at block 950 the application of the adjustment factor produces a final score predictive of whether or not an individual will suffer a fall event, e.g. a respective final fall score for each of the plurality of individuals.

Figure 10:
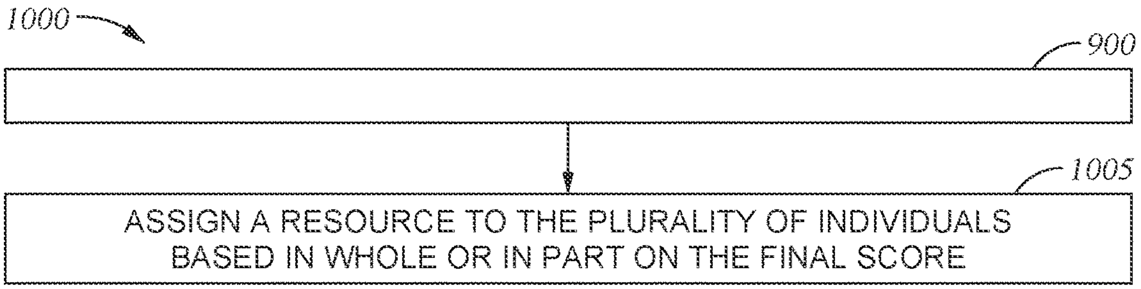
FIG. 10 is a process flow diagram for a method of utilizing a machine learning model, according to one or more implementations of the present disclosure.

FIG. 10 illustrates a flow diagram 1000 for assigning a resource to one or more individuals. In some implementations, flow diagram 1000 carries out one or more operations associated with flow 900. In some implementations, as shown, flow 1000 carries out all of the operations associated with the blocks of flow 900. In some implementations, a resource is assigned to the plurality of individuals, e.g. patients or residents, based in whole or in part on the generated final fall prediction score(s) 1005. Any suitable component of the present disclosure can be configured to provide one or more instructions to suggest a resource for one or more individuals associated with the received data, where the resource allocation can be based on a request from another user device or can be automatically made (to another device), e.g. via a network, based on the processing of the received data. A process or other suitable component can be configured to compare the fall prediction score with one or more conditions (if any), respectively, associated with the plurality of each individuals. In one or more implementations, a suitable component as described herein can be configured to associate a condition and/or preference to the fall prediction score. In some implementations, the suitable component as described herein can be configured to output a specific resource to each of the plurality of individuals if he or she has a particular condition and in relation to that condition if outputted fall prediction score exceeds a certain threshold. In some implementations, the suitable component as described herein can account for multiple conditions by performing any suitable mathematical operation, e.g., a sum, product, weighting or factorial increase based on the fall prediction scores of the plurality of individuals. In some implementations, a particular condition will automatically warrant at least one resource allocation irrespective of the fall prediction score of each individual, and the addition of other conditions can impact whether additional resources are allocated to a particular individual. In some implementations each condition can be associated with a particular threshold in relation to the fall prediction score and in relation to whether a particular resource or resource is allocated.

In some implementations, for example, the suitable component as described herein can be configured to suggest or allocate a resource based solely on the fall prediction scores, respectively, of each of the plurality of individuals. For example, if the score meets or exceeds a first threshold is met, $N_{t1}$ then a first resource is suggested, e.g., a soothing voice of a family member or pre-recorded music associated with a family member of a particular individual of the plurality of individuals is played over a loud speaker (e.g. instructing a resident to stay in place while medical assistance arrives). If the score meets or exceeds a second threshold $N_{t2}$, then another resource or an additional resource can be suggested, e.g. a wheelchair. If the score meets or exceeds a third threshold $N_{t3}$, then another or yet additional resource can be suggested, e.g. immediate medical assistance by a care provider (nurse, therapist, doctor, etc.) can be suggested. In some implementation, since a fall prediction score is based on data that is in part particular to an individual of the plurality of individuals, inherently, the resource allocation based on the fall prediction score is specific to a user. In some implementation, in order to more particularize a resource allocation to each of the plurality of individuals, respectively, suitable component as described herein can be configured to compare a fall prediction score associated with a particular condition associated with, respectively, each of the plurality of individuals. For example, any suitable component as described herein can be configured to suggest a particular resource based on fall prediction scores that are specific to particular conditions or are weighted based on the number and/or type of conditions. For example, condition 1, e.g. dementia, can have a weight $W_1$. If a particular individual of the plurality of individuals suffers from dementia and has a fall prediction score FS, then the product of $W_1$ and FS can be compared to particular threshold reference scores, e.g. $RS_1$, $RS_2$, $RS_3$, and so on, where if the product of $W_1$ and FS exceeds the one or more threshold or reference scores, then a resource corresponding to each reference score or a resource corresponding to the highest score is suggested. If multiple conditions are present, e.g. condition 1, e.g. dementia, and condition 2, e.g. a broken bone or fractured bone, then multiple weights, each corresponding to each condition, e.g. $W_1$ for dementia and $W_2$ for a broken or fractured bone, then $W_1$ and $W_2$ (and so on) can be applied to the fall prediction score FS to determine whether one or more resources should be assigned to the corresponding individual. In some implementations, the weights, e.g. $W_1$ and $W_2$, can be higher or lower based on their relevance as to whether or not an individual will suffer a fall relative to a condition, e.g. a sprained ankle can have a lower weight than a fractured hip.

In some implementations, each condition can correspond to a particular threshold, and if the threshold, e.g. $RS_1$, $RS_2$, and for the condition or conditions is not met, then no resource is assigned, and if the threshold for the condition or conditions is met, then each resource associated with the particular condition is suggested by suitable component as described herein configured as such. In some implementations, the threshold for one condition can be correlated to the condition presents a higher likelihood an individual will suffer a fall as result of the condition, e.g. a sprained ankle can have a lower threshold than a fractured hip. In some implementations, suitable component as described herein can be configured to coordinate with one or more sensing, audiovisual (e.g. camera), or other suitable devices to make a suggestion as to whether or not a resource should be provided. For example, if an individual of the plurality of individuals has a score that exceeds a certain threshold or exceeds a certain threshold relative to one or more conditions, and individual of the plurality of individuals already has the suggested allocation (e.g. by conducting a scan of a particular setting and performing any suitable audiovisual operation to detect the individual of the plurality of individuals and his or her surrounding and/or allocated resources), then no further allocation can be made. By way of another example, any suitable component as described herein can be configured suggest allocating or not allocating a resource based on a threshold being met or not met relative to a fall prediction score and one or more conditions, in addition to an audiovisual scan of a particular setting. If a resource allocation is suitable only in the case of movement, e.g. leg brace or wheel chair, for example, but the individual of the plurality of individuals is on his or her bed, then a particular resource allocation can be withheld as extraneous based on an audiovisual analysis of the care setting.

In some implementations, a condition warrants more than one resource allocation or a certain fall prediction score that is weighted by multiple conditions warrants more than one resource allocation. In some implementations, a certain condition can warrant a resource allocation irrespective of a fall prediction score, but a fall prediction score weighted by additional conditions can warrant an additional resource and/or a scan or other review of a care setting, e.g. by a sensor or camera, can warrant an additional resource assignment.

Figure 11:
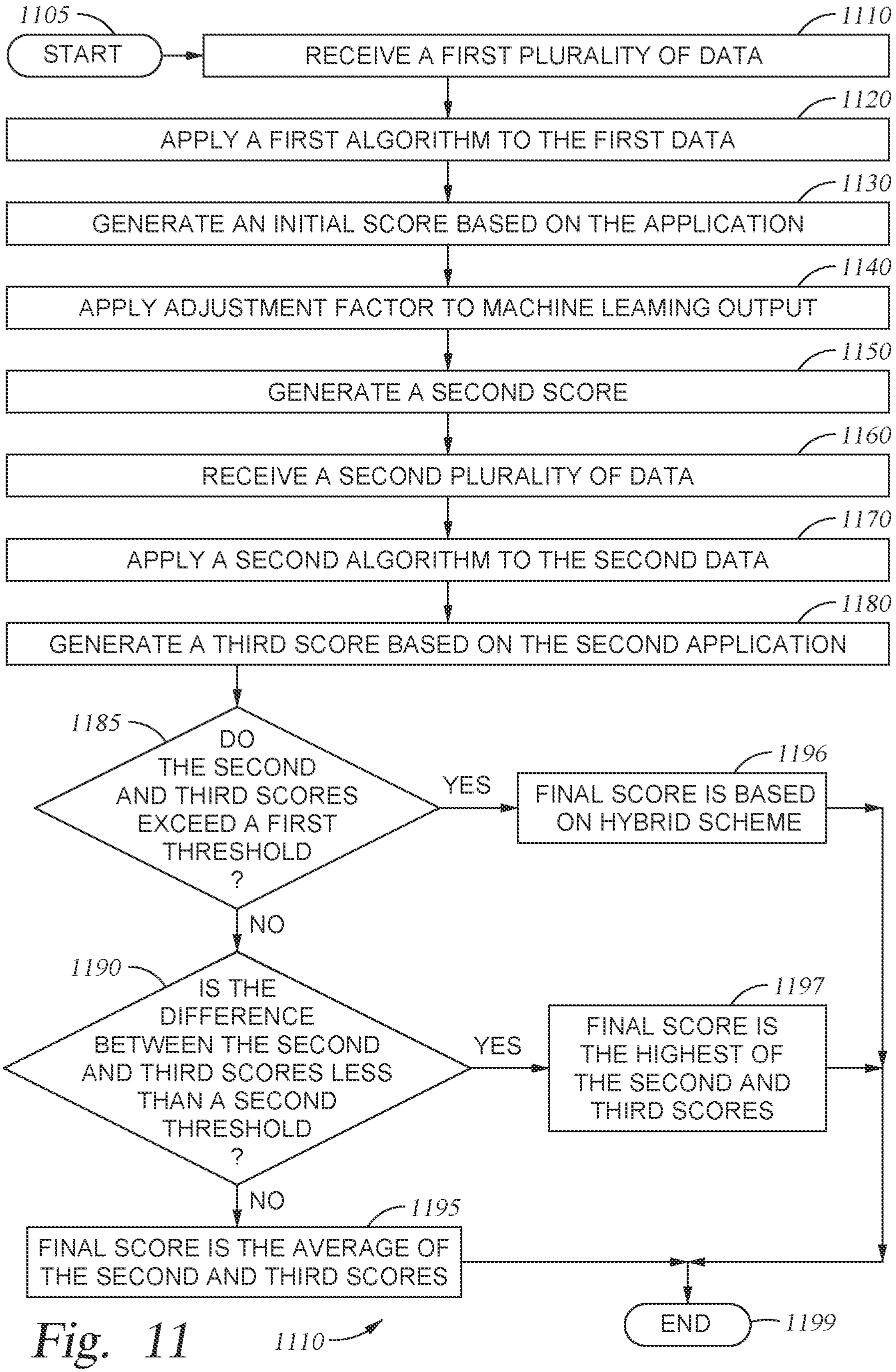
FIG. 11 is a process flow diagram for a method of utilizing a machine learning model, according to one or more implementations of the present disclosure

FIG. 11 illustrates a flow 1100 for training a machine learning model in accordance with various techniques associated with the present disclosure. In one or more implementations, the flow includes block 1105, e.g. the flow 1100 can begin therefrom. In one or more implementations, the flow 1100 includes block 1110, where any suitable computer system or component, e.g. system 100 and processors 114, receives a first plurality of data, e.g. medical data or other, associated with a first set of one or more individuals. Here, receiving can mean inputting the data by any means such as keying, or data transfer from a data set (e.g., MDS, ADS, and electronic medical records). In one or more implementations, the first plurality of medical data can include: i) active diagnosis information associated with the one or more individuals, e.g. recent diagnoses or diagnoses that refer to present or current medical conditions associated with one or more individuals, ii) active and new medication data (e.g. medication recently or currently being taken by the one or more individuals), and iii) ADL, MDS, and recent vitals of the one or more individuals.

In one or more implementations, the flow 1100 includes a block 1120 for applying a first algorithm to the first plurality of data. The first algorithm can be a hybrid machine learning algorithm as discussed with respect to FIGS. 7-9, where one or more static components and static dictionaries associated therewith process the active and new diagnostic data and the active medication data, and a dynamic component, e.g. neural network, process the ADL, MDS, and recent vital data. In one or more implementations, the flow includes block 1130 where the application of the first algorithm can generate a first score, where the first score is a prediction as to whether or not one or more of the one or more individuals will sustain a fall. The first score can be generated as described with respect to FIGS. 7-9, where with respect to one or more implementations, the first score is based on data i)-iii) and not additional data as discussed with some of the one or more implementations associated with FIGS. 7-9. In one or more implementations, an adjustment factor can be applied to the initial score, as show in block 1140 of flow 1100. In one or more implementations, the adjustment factor can be based on fall history data of the one or more individuals and/or other individuals, and that is part of or distinct from the first plurality of data, and where the adjustment factor can be based on the equations, structures and techniques discussed with respect to one or more individuals. In one or more implementations, the flow 1100 can include block 1150, where block 1150 generates a second score based on application of the adjustment component, and in one or more implementations, the second score corresponds to the final score with respect to the discussion associated with FIGS. 7-9.

In one or more implementations, flow 1100 includes block 1160, where block 1160 receives a second plurality of data associated with the one or more individuals. In one or more implementations, the second plurality of data is clinical data with specific data associated with the one or more individuals, and that is within a specific temporal range (e.g. 24-72 hours), where the second plurality of data can include balance data (e.g. balance tests administered to assess how well balanced each of the one or more individuals is), admission data (e.g. admission to a hospital, care facility within a specified time frame, e.g. 24-48 hours), mobility data (e.g. if a wheel chair, mechanical lift, or other assistance is required), psychiatric medication data 635*c* (e.g. where in one or more implementations, as discussed below, this can be a separate data category from active medication data 610*c*), vitality data, behavioral data (e.g. evidence of specific erratic behavior such as shaking), and continence data (e.g. changes in continence), and as may be referenced with respect to other implementation as described above, and where the data sources can further be based in whole or in part on predetermined forms as described herein.

In one or more implementations, flow 1100 includes applying a second algorithm or a portion of a second algorithm associate as per block 1170. In one or more implementations, as stated above and implied herein, experimentation and testing at one or more facilities has determined that utilizing an additional model or algorithm with specific data sources, e.g. real time data, that is specific to a particular individual or individuals can further generate a more accurate and tailored fall prediction score, which in turn can be used to provide a more appropriate prophylactic measure for one or more users. In one or more implementations, block 1170 includes all or part of this additional model. The additional model or algorithm can be a model that includes a logic component for determine which more formula or scheme to apply and a computational component for computing the formula or scheme. The second algorithm can be determined in part by correlation or probabilistic techniques that evaluated data associated with other individuals, e.g. distinct from the one or more individuals, to determine a weighting scheme for particular data sources, e.g. as discussed with respect to FIG. 6C. In one or more implementations, application of the second algorithm can include summing up the data multiplied by weights in relation to each data source. For example, if it is determined that a change or lack thereof in behavior is the least important, and the next important is a continence change, then the weight, e.g., Wc, for continence change can be Wb (the weight for behavioral changes) plus a factor N, and where the next important data source, e.g. nutritional changes (e.g. lack of eating) can be Wc+N. In order to optimize accuracy, "N" can be constant between some data sources, but can change if a data source is particularly important, e.g. the weight for a data source can be Wp+N+N2, where Wp is the weight for the data source immediately precedent in importance, and N2 is an additional additive to the value. In one or more implementations, factorial increases, e.g. N, 2N, 3N, etc. can be used in whole or in part. In one or more implementations, once the weights are determined, the computational, pursuant to block 1180, a third score (e.g. clinical score) is generated using the Equation 4.

The individual data categories, e.g. balance change, can be a "1" or "0" if a change in the particular category is detected or it can be a number based on threshold equations, e.g. as discussed above in reference to predetermined forms, where the initial number can be higher than one. In one or more implementations, the flow includes block 1185. If the both the Clinical Score (third score) and the second score (or fall risk model score) both exceed a certain threshold or value T, e.g. 50, then the following scheme is applied to generate final score pursuant to block 1196, where the final score is a hybrid of the second score and the third score using Equation 5. The greater of the two scores is added to the lesser of the two scores adjusted by a scaling factor, where the lesser of the two scores is multiplied by any suitable factor to reduce its value (e.g. based on a product, difference or a product and difference, etc.), and where the sum is divided by another scaling factor.

If the two scores are below the certain threshold T, then the flow 1100 includes block 1190. Pursuant to block 1190, if the second score and third score are within a certain range R1, e.g. the difference is small, then the final score, pursuant to block 1195, is the higher of the two scores.

If the two scores are beneath the certain threshold T, but the difference is greater than R1, then the flow 1100 includes block 1197 and the final score is an average of the scores. After this, the flow 1100 ends at block 1199.

In one or more implementations, since the overall flow 1100 includes both score based on a fall prediction stemming from whether previous falls have occurred and what the likelihood is that a fall will occur as a result therefrom, e.g. a final score of the first algorithm and reflected as the second score of flow 1100, and a clinical factor score produced by that is based on a scheme that accounts for clinical factors unique to the subject for which a score is to be determined, e.g. a third score of flow 1100 produced by the second algorithm of flow 1100, a more accurate result is generated, where said accurate result can be used to provide a superior prophylactic measure in relation to a potential fall for a patient or resident of a care facility or hospital, and where said accurate result is based on a first hybrid algorithm combined with a second static algorithm forming an overall hybrid algorithm, e.g. flow 1100.

In one or more implementations, as stated and implied herein, the data associated with FIG. 6C can also be based on predetermined forms to enhance accuracy and efficiency in relation to said score.

Example Computing Hardware

Figure 12:
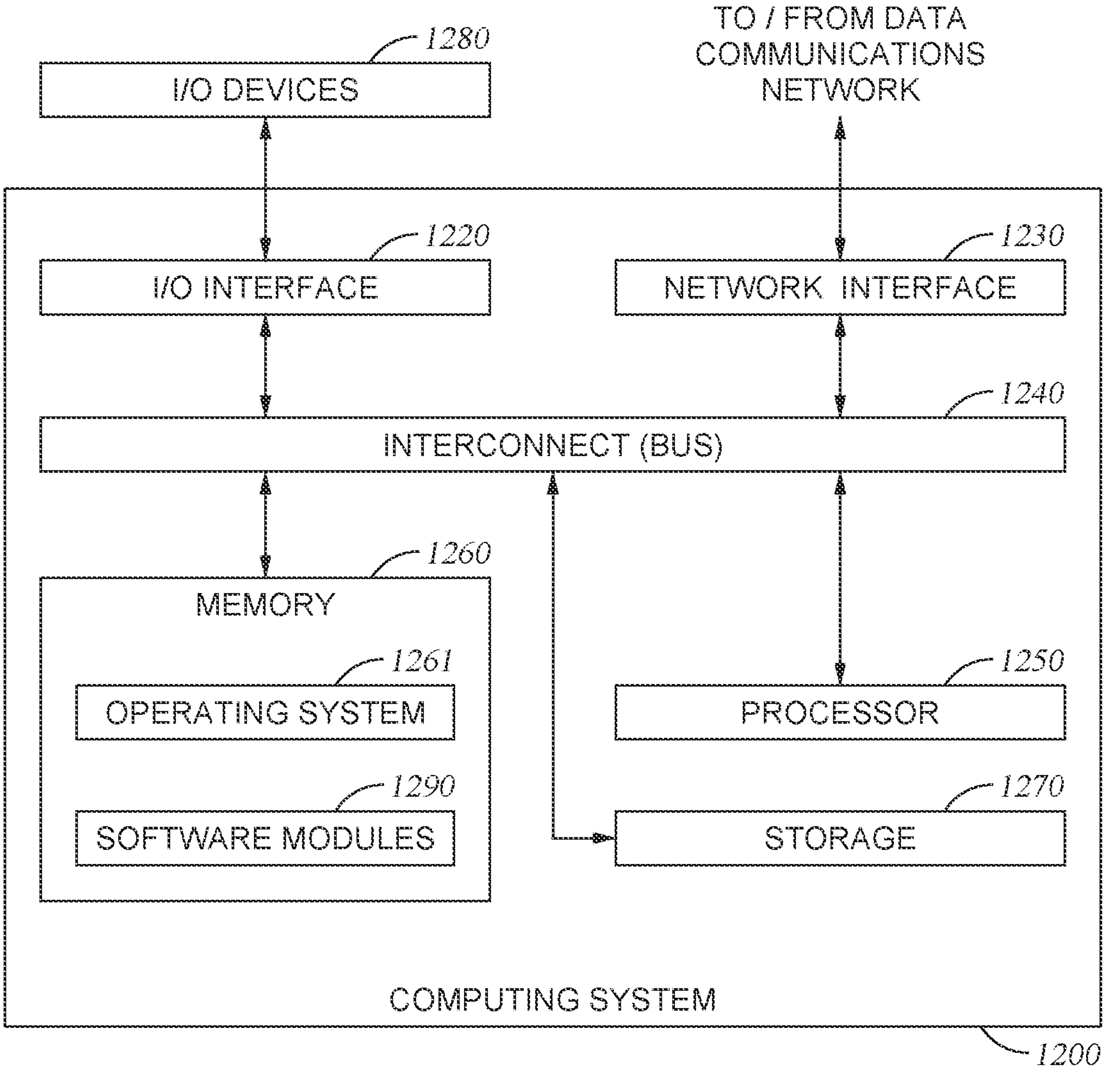
FIG. 12 illustrates a computing system, according to one embodiment.

FIG. 12 illustrates a computing system 1200, which may be used to implement the prediction system 100 in FIG. 1, or any other computing device described in the present disclosure. As shown, the computing system 1200 includes, without limitation, a computer processor 1250 (e.g., a central processing unit), a network interface 1230, and memory 1260. The computing system 1200 may also include an input/output (I/O) device interface 1220 connecting I/O devices 1280 (e.g., keyboard, display and mouse devices) to the computing system 1200.

The processor 1250 retrieves and executes programming instructions stored in the memory 1260 (e.g., a non-transitory computer readable medium). Similarly, the processor 1250 stores and retrieves application data residing in the memory 1260. An interconnect 1240 facilitates transmission, such as of programming instructions and application data, between the processor 1250, I/O device interface 1220, storage 1270, network interface 1230, and memory 1260. The processor 1250 is included to be representative of a single processor, multiple processors, a single processor having multiple processing cores, and the like. And the memory 1260 and the storage 1270 are generally included to be representative of volatile and non-volatile memory elements. For example, the memory 1260 and the storage 1270 can include random access memory and a disk drive storage device. Although shown as a single unit, the memory 1260 or the storage 1270 may be a combination of fixed and/or removable storage devices, such as magnetic disk drives, flash drives, removable memory cards or optical storage, network attached storage (NAS), or a storage area-network (SAN). The storage 1270 may include both local storage devices and remote storage devices accessible via the network interface 1230. If the computing system 1200 is used as the system 100 in FIG. 1, the weight assignor 140, model builder 150, ML trainer 160, event predictor 175, ML model 165, and trained ML model 180 may be software modules 1290 maintained in the memory 1260.

Further, the computing system 1200 is included to be representative of a physical computing system as well as virtual machine instances hosted on a set of underlying physical computing systems. Further still, although shown as a single computing device, one of ordinary skill in the art will recognize that the components of the computing system 1200 shown in FIG. 12 may be distributed across multiple computing systems connected by a data communications network.

As shown, the memory 1260 includes an operating system 1261. The operating system 1261 may facilitate receiving input from and providing output to various components.

ADDITIONAL CONSIDERATIONS

The preceding description is provided to enable any person skilled in the art to practice the various embodiments described herein. The examples discussed herein are not limiting of the scope, applicability, or embodiments set forth in the claims. Various modifications to these embodiments will be readily apparent to those skilled in the art, and the generic principles defined herein may be applied to other embodiments. For example, changes may be made in the function and arrangement of elements discussed without departing from the scope of the disclosure. Various examples may omit, substitute, or add various procedures or components as appropriate. For instance, the methods described may be performed in an order different from that described, and various steps may be added, omitted, or combined. Also, features described with respect to some examples may be combined in some other examples. For example, an apparatus may be implemented or a method may be practiced using any number of the aspects set forth herein. In addition, the scope of the disclosure is intended to cover such an apparatus or method that is practiced using other structure, functionality, or structure and functionality in addition to, or other than, the various aspects of the disclosure set forth herein. It should be understood that any aspect of the disclosure disclosed herein may be embodied by one or more elements of a claim.

As used herein, the word "exemplary" means "serving as an example, instance, or illustration." Any aspect described herein as "exemplary" is not necessarily to be construed as preferred or advantageous over other aspects.

As used herein, a phrase referring to "at least one of" a list of items refers to any combination of those items, including single members. As an example, "at least one of: a, b, or c" is intended to cover a, b, c, a-b, a-c, b-c, and a-b-c, as well as any combination with multiples of the same element (e.g., a-a, a-a-a, a-a-b, a-a-c, a-b-b, a-c-c, b-b, b-b-b, b-b-c, c-c, and c-c-c or any other ordering of a, b, and c).

As used herein, the term "determining" encompasses a wide variety of actions. For example, "determining" may include calculating, computing, processing, deriving, investigating, looking up (e.g., looking up in a table, a database or another data structure), ascertaining and the like. Also, "determining" may include receiving (e.g., receiving information), accessing (e.g., accessing data in a memory) and the like. Also, "determining" may include resolving, selecting, choosing, establishing and the like.

The methods disclosed herein comprise one or more steps or actions for achieving the methods. The method steps and/or actions may be interchanged with one another without departing from the scope of the claims. In other words, unless a specific order of steps or actions is specified, the order and/or use of specific steps and/or actions may be modified without departing from the scope of the claims. Further, the various operations of methods described above may be performed by any suitable means capable of performing the corresponding functions. The means may include various hardware and/or software component(s) and/or module(s), including, but not limited to a circuit, an application specific integrated circuit (ASIC), or processor. Generally, where there are operations illustrated in figures, those operations may have corresponding counterpart means-plus-function components with similar numbering.

The following claims are not intended to be limited to the embodiments shown herein, but are to be accorded the full scope consistent with the language of the claims. Within a claim, reference to an element in the singular is not intended to mean "one and only one" unless specifically so stated, but rather "one or more." Unless specifically stated otherwise, the term "some" refers to one or more. No claim element is to be construed under the provisions of 35 U.S.C. § 112(f) unless the element is expressly recited using the phrase "means for" or, in the case of a method claim, the element is recited using the phrase "step for." All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims.

Clause 1: A method comprising receiving a plurality of historical records, each comprising a sequence of entries and an indication whether an event occurred, for every entry in the sequences of entries: selecting a first entry in the sequences of entries; generating, for every record of the plurality of historical records, a ratio of a number of times the first entry is in the sequence of entries versus a total number of entries in the sequence; summing the ratios of the plurality of records indicating that the event did occur to yield a first summation (X); summing the ratios of the plurality of records indicating that the event did not occur to yield a second summation (Y); and generating a weight for the first entry using the following:

$$\frac{X}{Y} - \frac{Y}{X}.$$

The method also includes storing weights for the entries of the sequences of entries in a static model dictionary, and using the static model dictionary to at least one of (i) train a first machine learning (ML) model or (ii) provide input to a second ML model to predict whether the event will occur.

Clause 2: In addition to the clause 1, wherein each of the plurality of records corresponds to a different living organism, a different apparatus, or a different system.

Clause 3: In addition to the clauses 1 or 2, where the entries in the sequences of entries are codes defined according to a standard.

Clause 4: In addition to the clause 3, wherein the codes are diagnosis codes used to diagnosis a patient.

Clause 5: In addition to the clause 4, wherein the indication indicates whether or not the patient experienced the event, wherein the event is a medical event:

Clause 6: In addition to the clauses 3, 4, or 5, wherein the codes are repair or maintenance codes for an apparatus or a system, wherein the indication indicates whether or not the apparatus or the system experienced a repair or maintenance event Clause 7: In addition to the clauses 1, 2, 3, 4, 5, or 6, wherein the entries in the sequences of entries are medications that are, or were, prescribed to patients Clause 8: In addition to the clauses 1, 2, 3, 4, 5, 6, or 4, wherein larger, positive weights stored in the static model dictionary are correlated to the event occurring, while larger, negative weights stored in the static model dictionary are correlated to the event not occurring, and smaller negative and positive weights stored in the static model dictionary are weakly correlated to the event.

Clause 9: A method comprising providing a static model dictionary storing weights, each corresponding to a different entry, receiving a record comprising a sequence of entries, converting each entry in the sequence of entries to a weight using the static model dictionary, combining the weights to yield a combined weight, and using the combined weight to at least one of (i) train a first machine learning (ML) model or (ii) provide input to a second ML model to predict whether an event will occur.

Clause 10: In addition to the clause 9, wherein larger, positive weights stored in the static model dictionary are correlated to the event occurring, while larger, negative weights stored in the static model dictionary are correlated to the event not occurring, and smaller negative and positive weights stored in the static model dictionary are weakly correlated to the event Clause 11: In addition to the clauses 9 or 10, wherein the entries in the sequence of entries are codes defined according to a standard Clause 12: In addition to the clause 11, wherein the entries in the sequence of entries are one of: diagnosis codes, medication codes, repair codes, or maintenance codes Clause 13: In addition to the clauses 9, 10, 11, or 12, wherein combining the weights to yield the combined weight comprises averaging the weights according to a number of entries in the sequence of entries.

Clause 14: In addition to the clauses 9, 10, 11, 12 or 13, wherein the combined weight is used to train the first ML model, wherein the record comprises an indication of whether or not the event occurred, the method further comprising: training the first ML model using the indication.

Clause 15: In addition to the clauses 9, 10, 11, 12, 13, or 14, wherein the combined weight is used to provide input to the second ML model, the method further comprising: generating, using the second ML model, a likelihood the event will occur.

Clause 16: A non-transitory computer readable medium comprising instructions to be executed in a processor, the instructions when executed in the processor perform an operation, the operation comprising: providing a static model dictionary storing weights, each corresponding to a different entry; receiving a record comprising a sequence of entries; converting each entry in the sequence of entries to a weight using the static model dictionary; combining the weights to yield a combined weight; and using the combined weight to at least one of (i) train a first machine learning (ML) model or (ii) provide input to a second ML model to predict whether an event will occur.

Clause 17: In addition to the clause 16, wherein larger, positive weights stored in the static model dictionary are correlated to the event occurring, while larger, negative weights stored in the static model dictionary are correlated to the event not occurring, and smaller negative and positive weights stored in the static model dictionary are weakly correlated to the event.

Clause 18: In addition to the clauses 16 or 17, wherein the entries in the sequence of entries are codes defined according to a standard.

Clause 19: In addition to the clause 18, wherein the entries in the sequence of entries are one of: diagnosis codes, medication codes, repair codes, or maintenance codes.

Clause 20: In addition to the clauses 16, 17, 18, or 19, wherein combining the weights to yield the combined weight comprises averaging the weights according to a number of entries in the sequence of entries.

What is claimed is:

1. A method, comprising:

receiving a plurality of historical records, each comprising a sequence of medical entries and an indication whether an event occurred;

preprocessing the plurality of historical records using a scaler or encoder to transform the historical records into scaled or encoded representations;

for every entry in the sequences of medical entries:

selecting a first entry in the sequences of medical entries;

generating, for every record of the plurality of historical records, a ratio of a number of times the first entry is in the sequence of medical entries versus a total number of medical entries in the sequence;

summing the ratios of the plurality of historical records indicating that the event did occur to yield a first summation (X);

summing the ratios of the plurality of historical records indicating that the event did not occur to yield a second summation (Y); and generating a weight for the first entry using the following:

$$\frac{X}{Y} - \frac{Y}{X}$$

storing weights for the medical entries of the sequences of medical entries in a static model dictionary;

using the static model dictionary to at least one of (i) train a first machine learning (ML) model or (ii) provide input to a second ML model to predict whether the event will occur;

generating, based on a combined weight, a prediction that the event will occur; and in response to the prediction, assigning a clinical resource to a subject associated with the event and providing the prediction for display via a device interface for clinical use, wherein assigning the clinical resource comprises playing audio associated with the subject via a speaker, the audio comprising at least one of a soothing voice or pre-recorded music.

2. The method of claim 1, wherein each of the plurality of historical records corresponds to a different living organism, a different apparatus, or a different system.

3. The method of claim 1, where the medical entries in the sequences of medical entries are codes defined according to a standard.

4. The method of claim 3, wherein the codes are diagnosis codes used to diagnosis a patient.

5. The method of claim 4, wherein the indication indicates whether or not the patient experienced the event, wherein the event is a medical event.

6. The method of claim 3, wherein the codes are repair or maintenance codes for an apparatus or a system, wherein the indication indicates whether or not the apparatus or the system experienced a repair or maintenance event.

7. The method of claim 1, wherein the medical entries in the sequences of medical entries are medications that are, or were, prescribed to patients.

8. The method of claim 1, wherein larger, positive weights stored in the static model dictionary are correlated to the event occurring, while larger, negative weights stored in the static model dictionary are correlated to the event not occurring, and smaller negative and positive weights stored in the static model dictionary are weakly correlated to the event.

9. A method, comprising:

providing a static model dictionary storing weights, each corresponding to a different entry, wherein a weight is generated from a first summation that comprises ratios of a plurality of historical records indicating that a corresponding event did occur, and a second summation that comprises ratios of the plurality of historical records indicating that the corresponding event did not occur, and the weight is determined by forming two respective ratios between the first summation and the second summation and computing a difference between the two respective ratios;

receiving a record comprising a sequence of medical entries;

preprocessing the sequence of medical entries by applying a scaler or encoder to transform the medical entries into scaled or encoded representations;

converting each entry in the sequence of medical entries to a weight using the static model dictionary;

combining the weights to yield a combined weight; and using the combined weight to at least one of (i) train a first machine learning (ML) model or (ii) provide input to a second ML model to predict whether an event will occur;

generating, based on the combined weight, a prediction that the event will occur; and in response to the prediction, assigning a clinical resource to a subject associated with the event and providing the prediction for display via a device interface for clinical use, wherein assigning the clinical resource comprises playing audio associated with the subject via a speaker, the audio comprising at least one of a soothing voice or pre-recorded music.

10. The method of claim 9, wherein larger, positive weights stored in the static model dictionary are correlated to the event occurring, while larger, negative weights stored in the static model dictionary are correlated to the event not occurring, and smaller negative and positive weights stored in the static model dictionary are weakly correlated to the event.

11. The method of claim 9, wherein the medical entries in the sequence of medical entries are codes defined according to a standard.

12. The method of claim 11, wherein the medical entries in the sequence of medical entries are one of: diagnosis codes, medication codes, repair codes, or maintenance codes.

13. The method of claim 9, wherein combining the weights to yield the combined weight comprises averaging the weights according to a number of medical entries in the sequence of medical entries.

14. The method of claim 9 wherein the combined weight is used to train the first ML model, wherein the record comprises an indication of whether or not the event occurred, the method further comprising:

training the first ML model using the indication.

15. The method of claim 9, wherein the combined weight is used to provide input to the second ML model, the method further comprising:

generating, using the second ML model, a likelihood the event will occur.

16. A non-transitory computer readable medium comprising instructions to be executed in a processor, the instructions when executed in the processor perform an operation, the operation comprising:

providing a static model dictionary storing weights, each corresponding to a different entry, wherein a weight is generated from a first summation that comprises ratios of a plurality of historical records indicating that a corresponding event did occur, and a second summation that comprises ratios of the plurality of historical records indicating that the corresponding event did not occur, and the weight is determined by forming two respective ratios between the first summation and the second summation and computing a difference between the two respective ratios;

receiving a record comprising a sequence of medical entries;

preprocessing the sequence of medical entries by applying a scaler or encoder to transform the medical entries into scaled or encoded representations;

converting each entry in the sequence of medical entries to a weight using the static model dictionary;

combining the weights to yield a combined weight; and using the combined weight to at least one of (i) train a first machine learning (ML) model or (ii) provide input to a second ML model to predict whether an event will occur;

generating, based on the combined weight, a prediction that the event will occur; and in response to the prediction, assigning a clinical resource to a subject associated with the event and providing the prediction for display via a device interface for clinical use, wherein assigning the clinical resource comprises playing audio associated with the subject via a speaker, the audio comprising at least one of a soothing voice or pre-recorded music.

17. The non-transitory computer readable medium of claim 16, wherein larger, positive weights stored in the static model dictionary are correlated to the event occurring, while larger, negative weights stored in the static model dictionary are correlated to the event not occurring, and smaller negative and positive weights stored in the static model dictionary are weakly correlated to the event.

18. The non-transitory computer readable medium of claim 16, wherein the medical entries in the sequence of medical entries are codes defined according to a standard.

19. The non-transitory computer readable medium of claim 18, wherein the medical entries in the sequence of medical entries are one of: diagnosis codes, medication codes, repair codes, or maintenance codes.

20. The non-transitory computer readable medium of claim 16, wherein combining the weights to yield the combined weight comprises averaging the weights according to a number of medical entries in the sequence of medical entries.

* * * * *